United States Patent
Niemeyer et al.

(10) Patent No.: US 9,617,245 B2
(45) Date of Patent: Apr. 11, 2017

(54) PROCESS FOR PREPARING AN N-METHYL-SUBSTITUTED TRIACETONAMINE COMPOUND

(71) Applicants: Jochen Niemeyer, Essen (DE); Benjamin Willy, Duesseldorf (DE); Felix Nissen, Nottuln (DE); Manfred Neumann, Marl (DE); Guenter Kreilkamp, Marl (DE); Sabine Schering, Schermbeck (DE)

(72) Inventors: Jochen Niemeyer, Essen (DE); Benjamin Willy, Duesseldorf (DE); Felix Nissen, Nottuln (DE); Manfred Neumann, Marl (DE); Guenter Kreilkamp, Marl (DE); Sabine Schering, Schermbeck (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/003,978

(22) Filed: Jan. 22, 2016

(65) Prior Publication Data
US 2016/0214962 A1    Jul. 28, 2016

(30) Foreign Application Priority Data
Jan. 22, 2015    (EP) .................................... 15152068

(51) Int. Cl.
| C07D 401/14 | (2006.01) |
| C07D 211/74 | (2006.01) |
| C07D 211/58 | (2006.01) |
| C07D 211/46 | (2006.01) |

(52) U.S. Cl.
CPC .......... *C07D 401/14* (2013.01); *C07D 211/46* (2013.01); *C07D 211/58* (2013.01); *C07D 211/74* (2013.01)

(58) Field of Classification Search
CPC ............................ C07D 401/06; C07D 401/14
USPC .................................. 544/198; 546/186, 188
See application file for complete search history.

(56) References Cited

U.S. PATENT DOCUMENTS

| 4,110,331 A * | 8/1978 | Pettersson ............ C07D 211/60 546/185 |
| 4,435,572 A * | 3/1984 | Rapoport .............. C07C 255/00 546/216 |
| 2008/0251758 A1 | 10/2008 | Kirchhoff et al. |

FOREIGN PATENT DOCUMENTS

| EP | 0 302 020 A2 | 2/1989 |
| EP | 0 302 020 A3 | 2/1989 |
| EP | 0 729 947 A1 | 9/1996 |
| WO | WO 2004/089913 A1 | 10/2004 |
| WO | WO 2008/101979 A1 | 8/2008 |

OTHER PUBLICATIONS

Extended European Search Report issued Nov. 10, 2015 in Patent Application No. 15152068.1.
Extended European Search Report issued on Jun. 13, 2016 in Patent Application No. 16152152.1.
Jerzy Zakrzewski, et al., Efficient Synthesis of 4-ISOCYANO-2,2,6,6-Tetramethvlpiperidine-1-OXVL, Organic Preparations and Procedures International: The New Journal for Organic Synthesis, vol. 35, No. 4, XP055197816, 2003, pp. 386-390.
C. Harris, Untersuchungen über die cyclischen Acetonbasen, Justus Liebigs Annalen Der Chemie, vol. 417, XP002741350, 1918, 89 Pages (with partial English translation).
Extended European Search Report issued on Jun. 13, 2016 in Patent Application No. 16152159.6 (with English language translation of categories of cited documents).

* cited by examiner

*Primary Examiner* — Venkataraman Balasubramanian
(74) *Attorney, Agent, or Firm* — Oblon, McClelland, Maier & Neustadt, L.L.P.

(57) ABSTRACT

An N-methyl-substituted triacetonamine compound is prepared by reacting at least one triacetonamine compound (I) with formaldehyde under reductive conditions, in the presence of hydrogen and in the presence of a supported catalyst, wherein the supported catalyst contains at least one metal M, wherein the metal M is selected from the group consisting of V, Cr, Mo, Mn, Ni, Pd, Pt, Fe, Ru, Os, Co, Rh, Ir, and Cu.

16 Claims, No Drawings

PROCESS FOR PREPARING AN N-METHYL-SUBSTITUTED TRIACETONAMINE COMPOUND

BACKGROUND OF THE INVENTION

Field of the Invention

The present invention describes a process for preparing an N-methyl-substituted triacetonamine compound (triacetonamine="TAA"). The present invention particularly describes a process for methylating the nitrogen present in the ring, as shown, for example, in the reaction equation <1> (where R is, for example, an alkyl radical, an alkoxy radical, an amine radical or else an OH group):

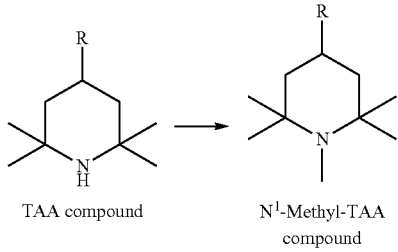

TAA compound     $N^1$-Methyl-TAA compound

Discussion of the Background

Methylated derivatives of 2,2,6,6-tetramethylpiperidine are employed with particular significance as "hindered amine light stabilizers" in particular. The methylation enables employment under acidic conditions as well. Commercial products having N-methylated 2,2,6,6-tetramethylpiperidine groups are, for example, Tinuvin® 292 [a mixture of 1-(methyl)-8-(1,2,2,6,6-pentamethyl-4-piperidinyl)sebacate and bis(1,2,2,6,6-pentamethyl-4-piperidinyl)sebacate] or Cyasorb® UV-3529 (CAS NUMBER 193098-40-7).

The related art discloses various methods of methylating amines.

For example, Kopka, I. E., et al., *J. Org. Chem.* 1980, 45, 4616-4622 and Minatti, A., et al., *J. Org. Chem.* 2007, 72, 9253-9258 describe the reaction of amines with methyl halides. This is shown in schematic form in reaction equation <2> (where R is a radical as defined in relation to reaction equation <1>):

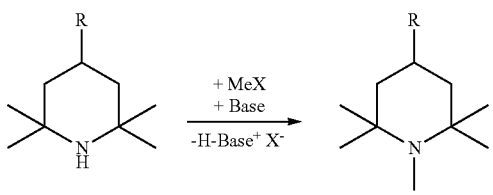

A disadvantage of the method shown in reaction equation <2> is that it is necessary to use at least one equivalent of a suitable base in addition to the methyl halide to release the product. This additionally leads to formation of the corresponding salts, which then arise as a waste product. An additional problem is that selective alkylation to give the tertiary amine is generally impossible since overalkylation to give the corresponding quaternary ammonium salt can take place.

A further method described in the related art is the Eschweiler-Clarke reaction (e.g. Lutz, W. B., et al., *J. Org. Chem.* 1962, 27, 1695-1703; EP 0 729 947 A1; WO 2004/072035 A1; WO 2005/123679 A2). In this method, the amine is reacted with formaldehyde in the presence of formic acid. The formic acid functions as a reducing agent and is converted to $CO_2$. In order that the reaction proceeds, one equivalent of base is generally additionally required. The reaction is illustrated schematically in the following reaction equation <3> (where R is a radical as defined in relation to reaction equation <1>):

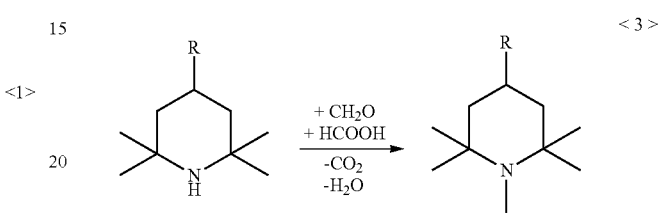

A disadvantage here is the need to use formic acid. Moreover, the use of the base again leads to generation of a corresponding waste stream.

A further means of N-methylation described in the related art (e.g. WO 2004/089913 A1, WO 2008/101979 A1) is the reaction with formaldehyde in the presence of borohydrides (e.g. sodium borohydride). The reaction is illustrated schematically in the following reaction equation <4> (where R is a radical as defined in relation to reaction equation <1>):

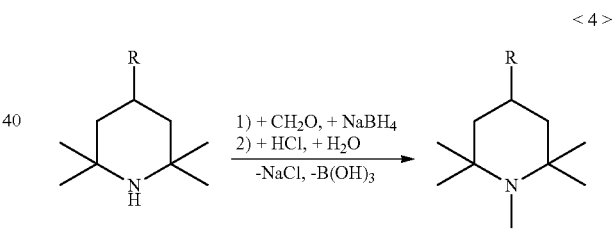

A disadvantage here is the need to use the borohydrides. The workup gives rise to large amounts of boric acid or boric acid derivatives as a waste stream.

SUMMARY OF THE INVENTION

The problem addressed by the present invention was therefore that of providing a process for preparing an N-methyl-substituted triacetonamine compound which does not have the aforementioned disadvantages.

The present invention relates to a process for preparing an N-methyl-substituted triacetonamine compound by reacting at least one triacetonamine compound (I) with formaldehyde under reductive conditions, in the presence of hydrogen and in the presence of a supported catalyst, wherein the supported catalyst comprises at least one metal M, wherein the metal M is selected from the group consisting of V, Cr, Mo, Mn, Ni, Pd, Pt, Fe, Ru, Os, Co, Rh, Ir, and Cu.

DETAILED DESCRIPTION OF THE INVENTION

A process which solves the problem described above has now surprisingly been found.

The present invention relates, in a first aspect, to a process according to the following Points 1.1 to 1.11:

1.1 Process for preparing an N-methyl-substituted triacetonamine compound, characterized in that at least one triacetonamine compound (I) is reacted with formaldehyde under reductive conditions, where the triacetonamine compound (I) is selected from the group consisting of the chemical structures (I-A), (I-B), (I-C), (I-D), (I-E), (I-F), (I-G), (I-H) with

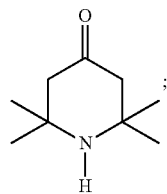
(I-A)

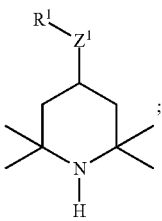
(I-B)

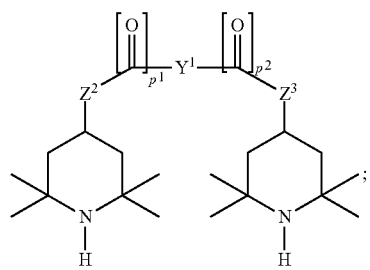
(I-C)

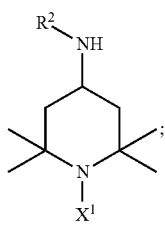
(I-D)

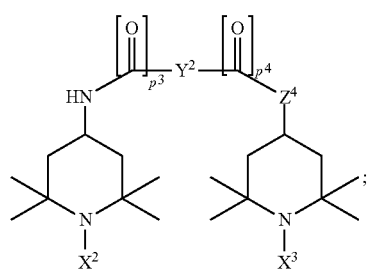
(I-E)

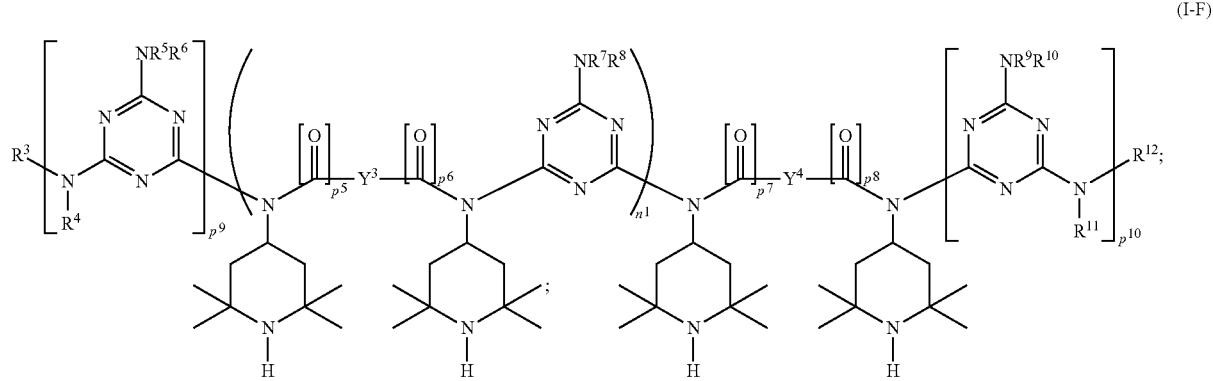
(I-F)

(I-G)

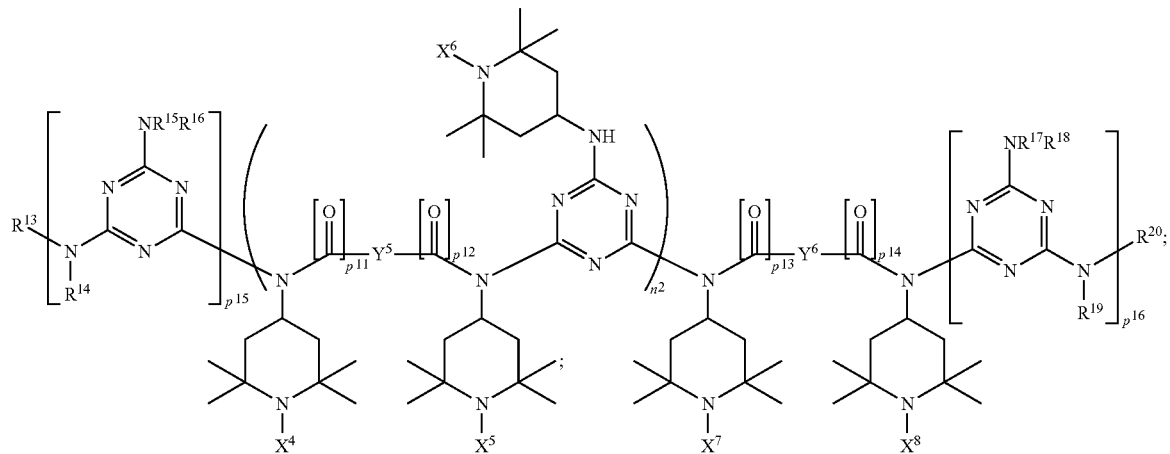

(I-H)

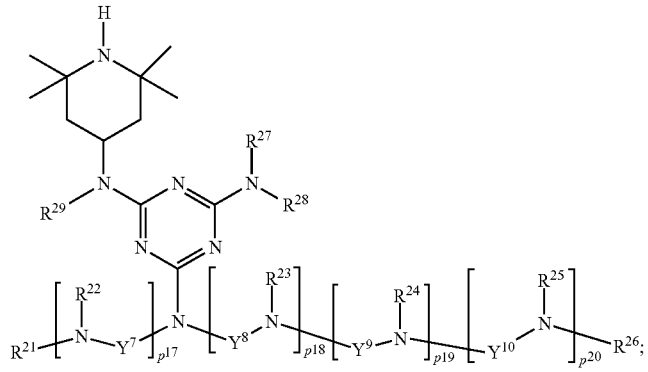

where $n^1$, $n^2$ are each independently an integer from the range of 1 to 20;

where $p^1$, $p^2$, $p^3$, $p^4$, $p^5$, $p^6$, $p^7$, $p^8$, $p^9$, $p^{10}$, $p^{11}$, $p^{12}$, $p^{13}$, $p^{14}$, $p^{15}$, $p^{16}$, $p^{17}$, $p^{18}$, $p^{19}$, $p^{20}$ are each independently 0 or 1;

where $X^1$ is selected from the group consisting of OH, —O., unbranched or branched alkyl group having 1 to 10 carbon atoms, unbranched or branched alkoxy group having 1 to 10 carbon atoms;

where $X^2$, $X^3$ are selected from the group consisting of hydrogen, OH, —O., unbranched or branched alkyl group having 1 to 10 carbon atoms, unbranched or branched alkoxy group having 1 to 10 carbon atoms, and where $X^2$, $X^3$ are each selected independently, with the exclusion of: $X^2$=$X^3$=hydrogen;

where $X^4$, $X^5$, $X^6$, $X^7$, $X^8$ are each independently selected from the group consisting of hydrogen, OH, —O., unbranched or branched alkyl group having 1 to 10 carbon atoms, unbranched or branched alkoxy group having 1 to 10 carbon atoms;

where $Y^1$, $Y^2$, $Y^3$, $Y^4$, $Y^5$, $Y^6$, $Y^7$, $Y^8$, $Y^9$, $Y^{10}$ are each independently selected from the group consisting of unbranched or branched alkylene group having 1 to 30 carbon atoms, divalent saturated hydrocarbyl group having 3 to 30 carbon atoms and having at least one saturated ring composed of 3 to 30 carbon atoms, divalent hydrocarbyl group having 6 to 30 carbon atoms, of which at least 6 carbon atoms are present in an aromatic system and the other carbon atoms, if present, are saturated, a bridging radical having a chemical structure selected from the group consisting of (i), (ii) with

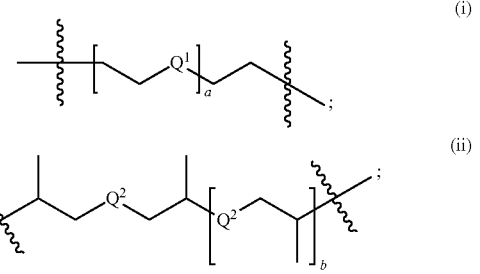

where $Q^1$, $Q^2$ are each independently selected from the group consisting of —O—, —S—, —NH— and NR'— with R'=unbranched or branched alkyl group having 1 to 6 carbon atoms, where a is an integer selected from the range of 1 to 50, where b is an integer selected from the range of 0 to 50, and where $Y^1$ may also be a direct bond if at least one of $p^1$ and $p^2$ has the value of 1, and where $Y^2$ may also be a direct bond if at least one of $p^3$ and $p^4$ has the value of 1, and where $Y^3$ may also be a direct bond if at least one of $p^5$ and $p^6$ has the value of 1, and where $Y^4$ may also be a direct bond if at least one of $p^7$ and $p^8$ has the value of 1, and where Y⁵ may also be a direct bond if at least one of p¹¹ and p¹² has the value of 1, and where Y⁶ may also be a direct bond if at least one of p¹³ and p¹⁴ has the value of 1;

and where $Z^1$, $Z^2$, $Z^3$, $Z^4$ are each independently selected from the group consisting of —O—, —S—, —NR³⁰—;

where the $R^1$, $R^2$, $R^3$, $R^4$, $R^5$, $R^6$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{30}$ radicals are each independently selected from the group consisting of hydrogen, unbranched or branched alkyl group which has 1 to 30 carbon atoms and in which at least one hydrogen radical may be replaced by a radical selected from the group consisting of —OH, —NH₂, —OCH₃, —OCH₂CH₃, —NH(CH₃), —N(CH₃)₂, —NH(CH₂CH₃), —N(CH₂CH₃)₂, —N(CH₃)(CH₂CH₃), unbranched or branched acyl group which has 1 to 30 carbon atoms and in which at least one hydrogen radical may be replaced by a radical selected from the group consisting of —OH, —NH₂, —OCH₃, —OCH₂CH₃, —NH(CH₃), —N(CH₃)₂, —NH(CH₂CH₃), —N(CH₂CH₃)₂, —N(CH₃)(CH₂CH₃);

a radical having a chemical structure selected from the group consisting of (iii), (iv), (v), (vi), (vii), (viii), (ix) with

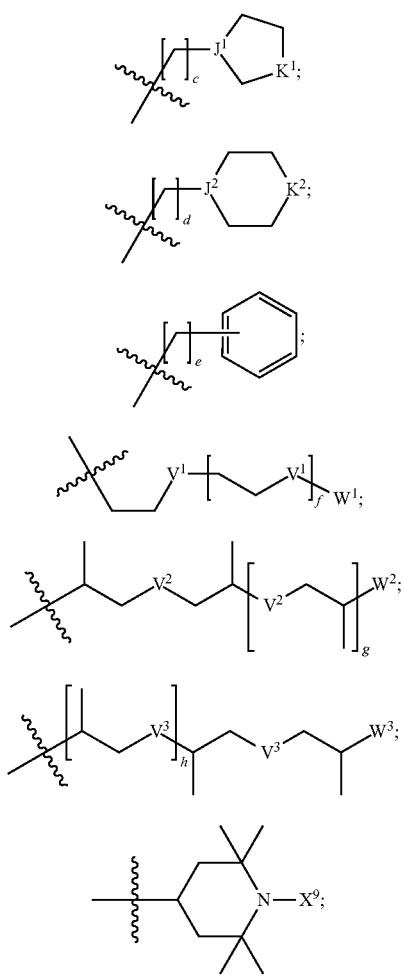

where $J^1$, $J^2$ are each independently selected from the group consisting of CH, N, where $K^1$, $K^2$ are each independently selected from the group consisting of —O—, —NH—, —N(CH₃)—, —N(CH₂CH₃)—, —S—, —CH₂—, where $V^1$, $V^2$, $V^3$ are each independently selected from the group consisting of —O—, —S—, —NH—, —NR″— with R″=unbranched or branched alkyl group having 1 to 6 carbon atoms, where $W^1$, $W^2$, $W^3$ are each independently selected from the group consisting of H, methyl, ethyl, where c, d, e, f, g, h are each independently an integer from the range of 0 to 50, where $X^9$ is selected from the group consisting of hydrogen, —OH, —O., unbranched or branched alkyl group having 1 to 10 carbon atoms, unbranched or branched alkoxy group having 1 to 10 carbon atoms, where, in the chemical structures (iii), (iv), (v), (vi), (vii), (viii), (ix), at least one hydrogen radical bonded to a carbon atom may be replaced by a radical selected from the group consisting of —OH, —NH₂, —OCH₃, —OCH₂CH₃, —NH(CH₃), —N(CH₃)₂, —NH(CH₂CH₃), —N(CH₂CH₃)₂, —N(CH₃)(CH₂CH₃);

where the $R^7$, $R^8$ radicals are each independently selected from the group consisting of hydrogen, unbranched or branched alkyl group which has 1 to 30 carbon atoms and in which at least one hydrogen radical may be replaced by a radical selected from the group consisting of —OH, —NH₂, —OCH₃, —OCH₂CH₃, —NH(CH₃), —N(CH₃)₂, —NH(CH₂CH₃), —N(CH₂CH₃)₂, —N(CH₃)(CH₂CH₃), unbranched or branched acyl group which has 1 to 30 carbon atoms and in which at least one hydrogen radical may be replaced by a radical selected from the group consisting of —OH, —NH₂, —OCH₃, —OCH₂CH₃, —NH(CH₃), —N(CH₃)₂, —NH(CH₂CH₃), —N(CH₂CH₃)₂, —N(CH₃)(CH₂CH₃);

and where, when $p^9=1$, —NR³R⁴ may also be a radical of the chemical structure (x), and where, when $p^{10}=1$, —NR¹¹R¹² may also be a radical of the chemical structure (x), and where the —NR⁵R⁶, —NR⁷R⁸, —NR⁹R¹⁰ radicals may each independently also be a radical of the chemical structure (x), where the chemical structure (x) is defined as follows:

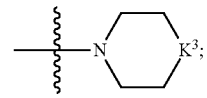

where $K^3$ is selected from the group consisting of —O—, —S—, —NH—, —N(CH₃)—, —N(CH₂CH₃)—, where $K^3$ is preferably —O—;

where the $R^{21}$, $R^{22}$, $R^{23}$, $R^{24}$, $R^{25}$, $R^{26}$ radicals are each independently selected from the group consisting of hydrogen, unbranched or branched alkyl group having 1 to 30 carbon atoms, a group having the chemical structure (xi) with

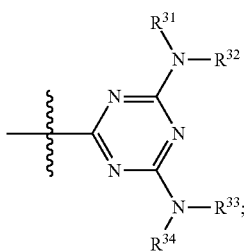
(xi)

where the $R^{27}$, $R^{28}$, $R^{29}$, $R^{31}$, $R^{32}$, $R^{33}$, $R^{34}$ radicals are each independently selected from the group consisting of
hydrogen,
unbranched or branched alkyl group which has 1 to 30 carbon atoms and in which at least one hydrogen radical may be replaced by a radical selected from the group consisting of
—OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$),
unbranched or branched acyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$);
a radical having a chemical structure selected from the group consisting of (xii), (xiii), (xiv), (xv), (xvi), (xvii), (xviii) with

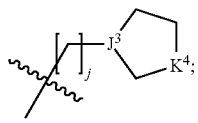
(xii)

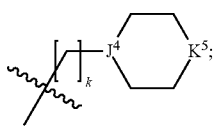
(xiii)

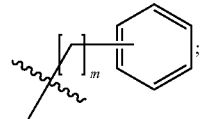
(xiv)

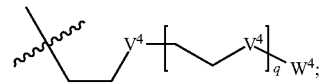
(xv)

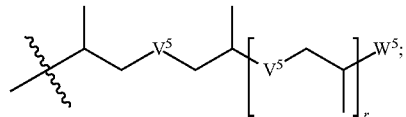
(xvi)

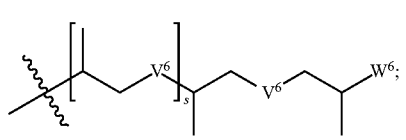
(xvii)

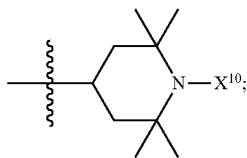
(xviii)

where $J^3$, $J^4$ are each independently selected from the group consisting of CH, N,
where $K^4$, $K^5$ are each independently selected from the group consisting of —O—, —NH—, —N(CH$_3$)—, —N(CH$_2$CH$_3$)—, —S—, —CH$_2$—,
where $V^4$, $V^5$, $V^6$ are each independently selected from the group consisting of —O—, —S—, —NH—, —NR'''— with R'''=unbranched or branched alkyl group having 1 to 6 carbon atoms,
where $W^4$, $W^5$, $W^6$ are each independently selected from the group consisting of H, methyl, ethyl,
where j, k, m, q, r, s are each independently an integer from the range of 0 to 50,
where $X^{10}$ is selected from the group consisting of hydrogen, —OH, —O., unbranched or branched alkyl group having 1 to 10 carbon atoms, unbranched or branched alkoxy group having 1 to 10 carbon atoms,
where, in the chemical structures (xii), (xiii), (xiv), (xv), (xvi), (xviii), at least one hydrogen radical bonded to a carbon atom may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$),
and with the proviso that $R^{21}$ and $R^{26}$, when $p^{17}=p^{18}=p^{19}=p^{20}=0$, may each independently also be a group of the chemical structure (xix) with

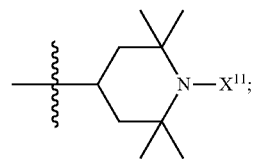
(xix)

where $X^{11}$ is selected from the group consisting of hydrogen, OH, —O., unbranched or branched alkyl group having 1 to 10 carbon atoms, unbranched or branched alkoxy group having 1 to 10 carbon atoms,
and wherein reductive conditions are established by reacting the at least one triacetonamine compound (I) with formaldehyde in the presence of hydrogen and in the presence of a supported catalyst, where the supported catalyst includes at least one metal M, where the metal M is selected from the group consisting of V, Cr, Mo, Mn, Ni, Pd, Pt, Fe, Ru, Os, Co, Rh, Ir, Cu.

1.2 Process according to point 1.1, where $p^1=p^2=p^3=p^4=p^5=p^6=p^7=p^8=p^{11}=p^{12}=p^{13}=p^{14}=0$ and where $p^9$, $p^{10}$, $p^{15}$, $p^{16}$, $p^{17}$, $p^{18}$, $p^{19}$, $p^{20}$ are each independently 0 or 1.

1.3 Process according to Point 1.1 or 1.2, where $Y^1$, $Y^2$, $Y^3$, $Y^4$, $Y^5$, $Y^6$, $Y^7$, $Y^8$, $Y^9$, $Y^{10}$ are each independently selected from the group consisting of unbranched or branched alkylene group having 1 to 30 carbon atoms, divalent saturated hydrocarbyl group having 3 to 30 carbon atoms and having at least one saturated ring composed of 3 to 30 carbon atoms.

1.4 Process according to one or more of Points 1.1 to 1.3, where the $R^1$, $R^2$, $R^3$, $R^4$, $R^5$, $R^6$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{30}$ radicals are each independently selected from the group consisting of hydrogen, unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$), a radical having a chemical structure (ix) with

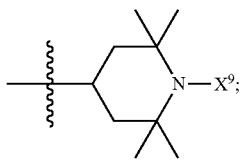

(ix)

where $X^9$ is selected from the group consisting of hydrogen, —OH, —O., unbranched or branched alkyl group having 1 to 10 carbon atoms, unbranched or branched alkoxy group having 1 to 10 carbon atoms;

where the $R^7$, $R^8$ radicals are each independently selected from the group consisting of hydrogen, unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$), and where, when $p^9$=1, —NR$^3$R$^4$ may also be a radical of the chemical structure (x), and where, when $p^{10}$=1, —NR$^{11}$R$^{12}$ may also be a radical of the chemical structure (x), and where the —NR$^5$R$^6$, —NR$^7$R$^8$, —NR$^9$R$^{10}$ radicals may each independently also be a radical of the chemical structure (x), where the chemical structure (x) is defined as follows:

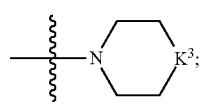

(x)

where $K^3$ is selected from the group consisting of —O—, —S—, —NH—, —N(CH$_3$)—, —N(CH$_2$CH$_3$)—, where $K^3$ is preferably —O—;

where the $R^{21}$, $R^{22}$, $R^{23}$, $R^{24}$, $R^{25}$, $R^{26}$ radicals are each independently selected from the group consisting of hydrogen, unbranched or branched alkyl group having 1 to 30 carbon atoms, a group having the chemical structure (xi) with

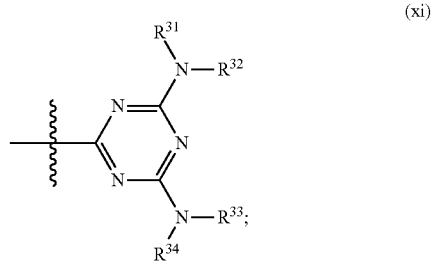

(xi)

where the $R^{27}$, $R^{28}$, $R^{29}$, $R^{31}$, $R^{32}$, $R^{33}$, $R^{34}$ radicals are each independently selected from the group consisting of hydrogen, unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$), a radical having a chemical structure (xviii) with

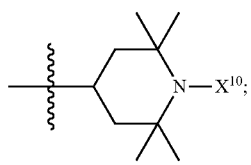

(xviii)

where $X^{10}$ is selected from the group consisting of hydrogen, —OH, —O., unbranched or branched alkyl group having 1 to 10 carbon atoms, unbranched or branched alkoxy group having 1 to 10 carbon atoms, and with the proviso that $R^{21}$ and $R^{26}$, when $p^{17}$=$p^{18}$=$p^{19}$=$p^{20}$=0, may each independently also be a group of the chemical structure (xix) with

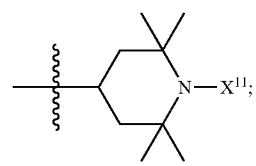

(xix)

where $X^{11}$ is selected from the group consisting of hydrogen, OH, —O., unbranched or branched alkyl group having 1 to 10 carbon atoms, unbranched or branched alkoxy group having 1 to 10 carbon atoms.

1.5 Process according to one or more of Points 1.1 to 1.4, where $X^4$=$X^5$=$X^6$=$X^7$=$X^8$=$X^9$=$X^{10}$=$X^{11}$ hydrogen.

1.6 Process according to one or more of Points 1.1 to 1.5, where the triacetonamine compound (I) is selected from the group consisting of the chemical structures (I-A), (I-B), (I-C), (I-D), (I-E).

1.7 Process according to one or more of Points 1.1 to 1.6, where the triacetonamine compound (I) is selected from the group consisting of the chemical structures (I-A), (I-B), (I-D), and where $Z^1$ is selected from the group consisting of —O—, —S—, —NR$^{30}$—;

where the $R^1$, $R^2$, $R^{30}$ radicals are each independently selected from the group consisting of
hydrogen,
unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$).

1.8 Process according to one or more of Points 1.1 to 1.7, where the triacetonamine compound (I) is selected from the group consisting of the chemical structures (I-A), (I-B), (I-D)
and where $Z^1$ is selected from the group consisting of —O—, —NR$^{30}$—;
where the $R^1$, $R^2$, $R^{30}$ radicals are each independently selected from the group consisting of
hydrogen,
unbranched or branched alkyl group having 1 to 12 carbon atoms, preferably 1 to 6 carbon atoms.

1.9 Process according to one or more of Points 1.1 to 1.8, wherein formaldehyde is used as a gas, as an aqueous solution or as a solid, preferably as an aqueous solution or as a solid, more preferably as an aqueous solution.

1.10 Process according to one or more of Points 1.1 to 1.9, wherein the at least one triacetonamine compound (I) is reacted with formaldehyde under reductive conditions in at least one solvent, where the solvent is selected from the group consisting of aliphatic solvents, aromatic solvents, ethers, halogenated solvents, amides, thio compounds, carboxylic acids, alcohols, water.

1.11 Process according to one or more of Points 1.1 to 1.10, wherein the at least one triacetonamine compound (I) is reacted with formaldehyde under reductive conditions at a temperature in the range from 20° C. to 350° C. and a pressure in the range from 2 bar to 500 bar.

The present invention relates, in a second aspect, to a process according to the following Points 2.1 to 2.4.

2.1 Process for preparing an N-methyl-substituted triacetonamine compound, characterized in that a triacetonamine compound (I) is reacted with formaldehyde under reductive conditions,
where the triacetonamine compound (I) has the chemical structure (I-A) with

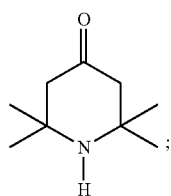

(I-A)

and wherein reductive conditions are established by reacting the at least one triacetonamine compound (I) with formaldehyde in the presence of hydrogen and in the presence of a supported catalyst, where the supported catalyst includes at least one metal M, where the metal M is selected from the group consisting of V, Cr, Mo, Mn, Ni, Pd, Pt, Fe, Ru, Os, Co, Rh, Ir, Cu.

2.2 Process according to Point 2.1, wherein formaldehyde is used as a gas, as an aqueous solution or as a solid, preferably as an aqueous solution or as a solid, more preferably as an aqueous solution.

2.3 Process according to one or more of Points 2.1 to 2.2, wherein the triacetonamine compound (I) is reacted with formaldehyde under reductive conditions in at least one solvent, where the solvent is selected from the group consisting of aliphatic solvents, aromatic solvents, ethers, halogenated solvents, amides, thio compounds, carboxylic acids, alcohols, water.

2.4 Process according to one or more of Points 2.1 to 2.3, wherein the triacetonamine compound (I) is reacted with formaldehyde under reductive conditions at a temperature in the range from 20° C. to 350° C. and a pressure in the range from 2 bar to 500 bar.

The present invention relates, in a third aspect, to a process according to the following Points 3.1 to 3.8.

3.1 Process for preparing an N-methyl-substituted triacetonamine compound,
characterized in that at least one triacetonamine compound (I) is reacted with formaldehyde under reductive conditions,
where the triacetonamine compound (I) has the chemical structure (I-B) with

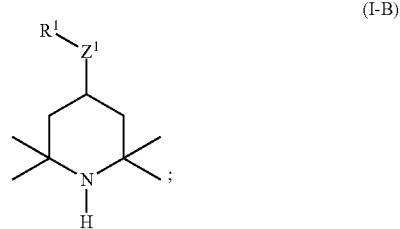

(I-B)

where $Z^1$ is selected from the group consisting of —O—, —S—, —NR$^{30}$—;
where the $R^1$, $R^{30}$ radicals are each independently selected from the group consisting of
hydrogen,
unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$),
unbranched or branched acyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$),
a radical having a chemical structure selected from the group consisting of (iii), (iv), (v), (vi), (vii), (viii), (ix) with

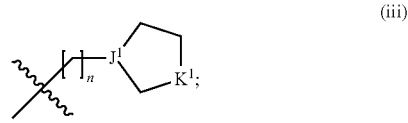

(iii)

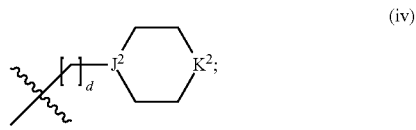

(iv)

-continued

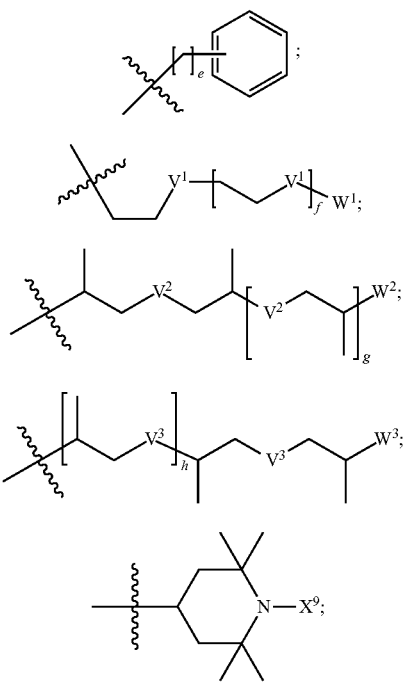

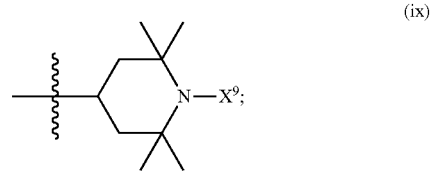

where $J^1$, $J^2$ are each independently selected from the group consisting of CH, N, where $K^1$, $K^2$ are each independently selected from the group consisting of —O—, —NH—, —N(CH$_3$)—, —N(CH$_2$CH$_3$)—, —S—, —CH$_2$—, where $V^1$, $V^2$, $V^3$ are each independently selected from the group consisting of —O—, —S—, —NH—, —NR"— with R"=unbranched or branched alkyl group having 1 to 6 carbon atoms, where $W^1$, $W^2$, $W^3$ are each independently selected from the group consisting of H, methyl, ethyl, where c, d, e, f, g, h are each independently an integer from the range of 0 to 50, where $X^9$ is selected from the group consisting of hydrogen, —OH, —O., unbranched or branched alkyl group having 1 to 10 carbon atoms, unbranched or branched alkoxy group having 1 to 10 carbon atoms, where, in the chemical structures (iii), (iv), (v), (vi), (viii), (ix), at least one hydrogen radical bonded to a carbon atom may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$), and wherein reductive conditions are established by reacting the at least one triacetonamine compound (I) with formaldehyde in the presence of hydrogen and in the presence of a supported catalyst, where the supported catalyst includes at least one metal M, where the metal M is selected from the group consisting of V, Cr, Mo, Mn, Ni, Pd, Pt, Fe, Ru, Os, Co, Rh, Ir, Cu.

3.2 Process according to Point 3.1, where the $R^1$, $R^{30}$ radicals are each independently selected from the group consisting of hydrogen, unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$), a radical having a chemical structure (ix) with where $X^9$ is selected from the group consisting of hydrogen, —OH, —O., unbranched or branched alkyl group having 1 to 10 carbon atoms, unbranched or branched alkoxy group having 1 to 10 carbon atoms.

3.3 Process according to Point 3.1 or 3.2, where $X^9$=hydrogen.

3.4 Process according to one or more of Points 3.1 to 3.3, where the $R^1$, $R^{30}$ radicals are each independently selected from the group consisting of hydrogen, unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$).

3.5 Process according to one or more of Points 3.1 to 3.4, where $Z^1$ is selected from the group consisting of —O—, —NR$^{30}$—;

where the $R^1$, $R^{30}$ radicals are each independently selected from the group consisting of hydrogen, unbranched or branched alkyl group having 1 to 12 and preferably 1 to 6 carbon atoms.

3.6 Process according to one or more of Points 3.1 to 3.5, wherein formaldehyde is used as a gas, as an aqueous solution or as a solid, preferably as an aqueous solution or as a solid, more preferably as an aqueous solution.

3.7 Process according to one or more of Points 3.1 to 3.6, wherein the at least one triacetonamine compound (I) is reacted with formaldehyde under reductive conditions in at least one solvent, where the solvent is selected from the group consisting of aliphatic solvents, aromatic solvents, ethers, halogenated solvents, amides, thio compounds, carboxylic acids, alcohols, water.

3.8 Process according to one or more of Points 3.1 to 3.7, wherein the at least one triacetonamine compound (I) is reacted with formaldehyde under reductive conditions at a temperature in the range from 20° C. to 350° C. and a pressure in the range from 2 bar to 500 bar.

The present invention relates, in a fourth aspect, to a process according to the following Points 4.1 to 4.10.

4.1 Process for preparing an N-methyl-substituted triacetonamine compound, characterized in that at least one triacetonamine compound (I) is reacted with formaldehyde under reductive conditions, where the triacetonamine compound (I) has the chemical structure (I-C) with (I-C)

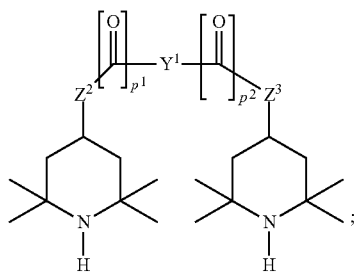

where $p^1$, $p^2$ are each independently 0 or 1;
where $Y^1$ is selected from the group consisting of
unbranched or branched alkylene group having 1 to 30 carbon atoms,
divalent saturated hydrocarbyl group having 3 to 30 carbon atoms and having at least one saturated ring composed of 3 to 30 carbon atoms,
divalent hydrocarbyl group having 6 to 30 carbon atoms, of which at least 6 carbon atoms are present in an aromatic system and the other carbon atoms, if present, are saturated,
a bridging radical having a chemical structure selected from the group consisting of (i), (ii) with

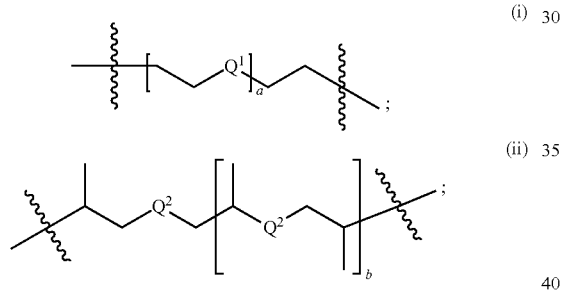

where
$Q^1$, $Q^2$ are each independently selected from the group consisting of —O—, —S—, —NH— and —NR'— with R'=unbranched or branched alkyl group having 1 to 6 carbon atoms,
where a is an integer selected from the range of 1 to 50,
where b is an integer selected from the range of 0 to 50,
and where $Y^1$ may also be a direct bond if at least one of $p^1$ and $p^2$ has the value of 1,
and where $Z^2$, $Z^3$ are each independently selected from the group consisting of —O—, —S—, —NR$^{30}$—;
where the R$^{30}$ radical is selected from the group consisting of
hydrogen,
unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$),
unbranched or branched acyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$);

a radical having a chemical structure selected from the group consisting of (iii), (iv), (v), (vi), (vii), (viii), (ix) with

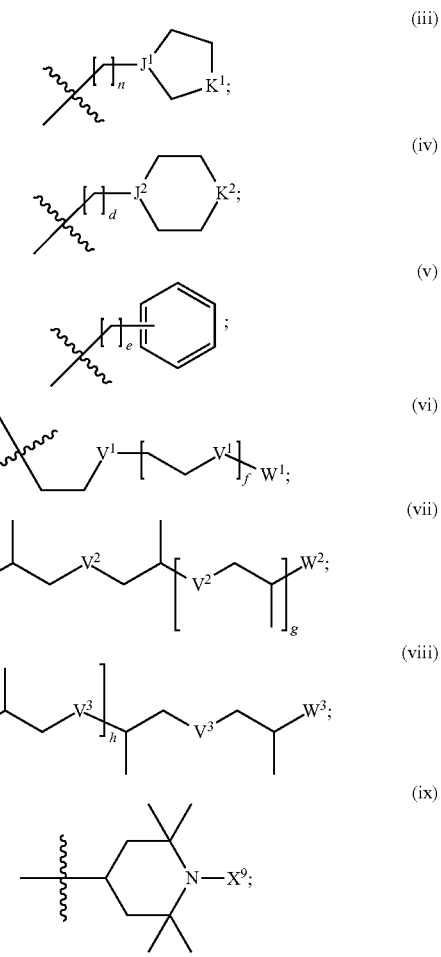

where $J^1$, $J^2$ are each independently selected from the group consisting of CH, N,
where $K^1$, $K^2$ are each independently selected from the group consisting of —O—, —NH—, —N(CH$_3$)—, —N(CH$_2$CH$_3$)—, —S—, —CH$_2$—,
where $V^1$, $V^2$, $V^3$ are each independently selected from the group consisting of —O—, —S—, —NH—, —NR"— with R"=unbranched or branched alkyl group having 1 to 6 carbon atoms,
where $W^1$, $W^2$, $W^3$ are each independently selected from the group consisting of H, methyl, ethyl,
where c, d, e, f, g, h are each independently an integer from the range of 0 to 50,
where $X^9$ is selected from the group consisting of hydrogen, —OH, —O., unbranched or branched alkyl group having 1 to 10 carbon atoms, unbranched or branched alkoxy group having 1 to 10 carbon atoms,
where, in the chemical structures (iii), (iv), (v), (vi), (vii), (viii), (ix), at least one hydrogen radical bonded to a carbon atom may be replaced by a radical selected from the group consisting of
—OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$),
and wherein reductive conditions are established by reacting the at least one triacetonamine compound (I) with formaldehyde in the presence of hydrogen and in the presence of a supported catalyst, where the supported catalyst includes at least one metal M, where the metal M is selected from the group consisting of V, Cr, Mo, Mn, Ni, Pd, Pt, Fe, Ru, Os, Co, Rh, Ir, Cu.

4.2 Process according to Point 4.1, where $p^1=p^2=0$.

4.3 Process according to Point 4.1 or 4.2, where
$Y^1$ is selected from the group consisting of
unbranched or branched alkylene group having 1 to 30 carbon atoms,
divalent saturated hydrocarbyl group having 3 to 30 carbon atoms and having at least one saturated ring composed of 3 to 30 carbon atoms.

4.4 Process according to one or more of Points 4.1 to 4.3, where the $R^{30}$ radical is selected from the group consisting of
hydrogen,
unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$),
a radical having a chemical structure (ix) with

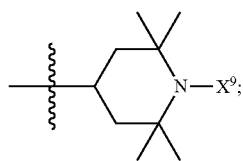

(ix)

where $X^9$ is selected from the group consisting of hydrogen, —OH, —O., unbranched or branched alkyl group having 1 to 10 carbon atoms, unbranched or branched alkoxy group having 1 to 10 carbon atoms.

4.5 Process according to one or more of Points 4.1 to 4.4, where $X^9$=hydrogen.

4.6 Process according to one or more of Points 4.1 to 4.5, where the $R^{30}$ radical is selected from the group consisting of
hydrogen,
unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$).

4.7 Process according to one or more of Points 4.1 to 4.6, where the $R^{30}$ radical is selected from the group consisting of
hydrogen,
unbranched or branched alkyl group having 1 to 12 and preferably 1 to 6 carbon atoms.

4.8 Process according to one or more of Points 4.1 to 4.7, wherein formaldehyde is used as a gas, as an aqueous solution or as a solid, preferably as an aqueous solution or as a solid, more preferably as an aqueous solution.

4.9 Process according to one or more of Points 4.1 to 4.8, wherein the at least one triacetonamine compound (I) is reacted with formaldehyde under reductive conditions in at least one solvent, where the solvent is selected from the group consisting of aliphatic solvents, aromatic solvents, ethers, halogenated solvents, amides, thio compounds, carboxylic acids, alcohols, water.

4.10 Process according to one or more of Points 4.1 to 4.9, wherein the at least one triacetonamine compound (I) is reacted with formaldehyde under reductive conditions at a temperature in the range from 20° C. to 350° C. and a pressure in the range from 2 bar to 500 bar.

The present invention relates, in a fifth aspect, to a process according to the following Points 5.1 to 5.8.

5.1 Process for preparing an N-methyl-substituted triacetonamine compound,
characterized in that at least one triacetonamine compound (I) is reacted with formaldehyde under reductive conditions,
where the triacetonamine compound (I) has the chemical structures (I-D) with

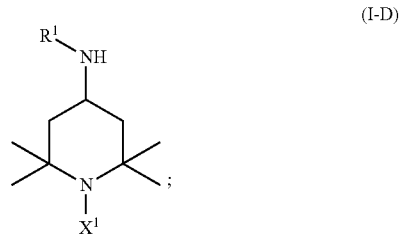

(I-D)

where $X^1$ is selected from the group consisting of OH, —O., unbranched or branched alkyl group having 1 to 10 carbon atoms, unbranched or branched alkoxy group having 1 to 10 carbon atoms;
where the $R^2$ radical is selected from the group consisting of
hydrogen,
unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$),
unbranched or branched acyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$),
a radical having a chemical structure selected from the group consisting of (iii), (iv), (v), (vi), (vii), (viii), (ix) with

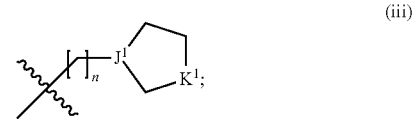

(iii)

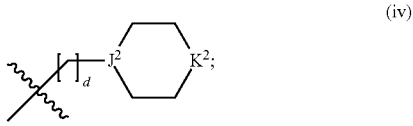

(iv)

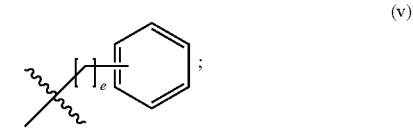

(v)

21

-continued

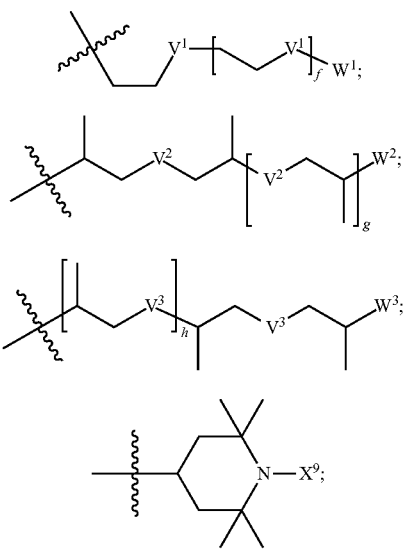

(vi)

(vii)

(viii)

(ix)

where $J^1$, $J^2$ are each independently selected from the group consisting of CH, N, where $K^1$, $K^2$ are each independently selected from the group consisting of —O—, —NH—, —N(CH$_3$)—, —N(CH$_2$CH$_3$)—, —S—, —CH$_2$—, where $V^1$, $V^2$, $V^3$ are each independently selected from the group consisting of —O—, —S—, —NH—, —NR"— with R"=unbranched or branched alkyl group having 1 to 6 carbon atoms, where $W^1$, $W^2$, $W^3$ are each independently selected from the group consisting of H, methyl, ethyl, where c, d, e, f, g, h are each independently an integer from the range of 0 to 50, where $X^9$ is selected from the group consisting of hydrogen, —OH, —O., unbranched or branched alkyl group having 1 to 10 carbon atoms, unbranched or branched alkoxy group having 1 to 10 carbon atoms, where, in the chemical structures (iii), (iv), (v), (vi), (vii), (viii), (ix), at least one hydrogen radical bonded to a carbon atom may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$), and wherein reductive conditions are established by reacting the at least one triacetonamine compound (I) with formaldehyde in the presence of hydrogen and in the presence of a supported catalyst, where the supported catalyst includes at least one metal M, where the metal M is selected from the group consisting of V, Cr, Mo, Mn, Ni, Pd, Pt, Fe, Ru, Os, Co, Rh, Ir, Cu.

5.2 Process according to Point 5.1, where the $R^2$ radical is selected from the group consisting of hydrogen, unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$),

22 a radical having a chemical structure (ix) with

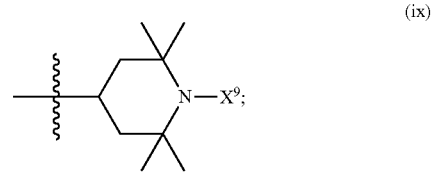

(ix)

where $X^9$ is selected from the group consisting of hydrogen, —OH, —O., unbranched or branched alkyl group having 1 to 10 carbon atoms, unbranched or branched alkoxy group having 1 to 10 carbon atoms.

5.3 Process according to Point 5.1 or 5.2, where $X^9$=hydrogen.

5.4 Process according to one or more of Points 5.1 to 5.3, where the $R^2$ radical is selected from the group consisting of hydrogen, unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$).

5.5 Process according to one or more of Points 5.1 to 5.4, where the $R^2$ radical is selected from the group consisting of hydrogen, unbranched or branched alkyl group having 1 to 12 and preferably 1 to 6 carbon atoms.

5.6 Process according to one or more of Points 5.1 to 5.5, wherein formaldehyde is used as a gas, as an aqueous solution or as a solid, preferably as an aqueous solution or as a solid, more preferably as an aqueous solution.

5.7 Process according to one or more of Points 5.1 to 5.6, wherein the at least one triacetonamine compound (I) is reacted with formaldehyde under reductive conditions in at least one solvent, where the solvent is selected from the group consisting of aliphatic solvents, aromatic solvents, ethers, halogenated solvents, amides, thio compounds, carboxylic acids, alcohols, water.

5.8 Process according to one or more of Points 5.1 to 5.7, wherein the at least one triacetonamine compound (I) is reacted with formaldehyde under reductive conditions at a temperature in the range from 20° C. to 350° C. and a pressure in the range from 2 bar to 500 bar.

The present invention relates, in a sixth aspect, to a process according to the following Points 6.1 to 6.10.

6.1 Process for preparing an N-methyl-substituted triacetonamine compound, characterized in that at least one triacetonamine compound (I) is reacted with formaldehyde under reductive conditions, where the triacetonamine compound (I) has the chemical structures (I-E) with

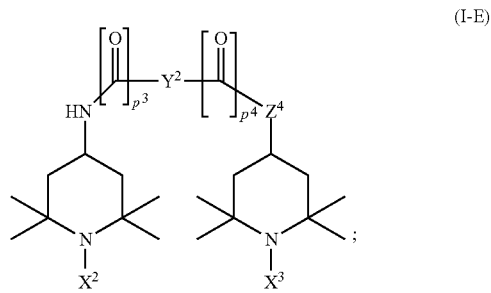

(I-E)

where $p^3$, $p^4$ are each independently 0 or 1;

where $X^2$, $X^3$ are selected from the group consisting of hydrogen, OH, —O., unbranched or branched alkyl group having 1 to 10 carbon atoms, unbranched or branched alkoxy group having 1 to 10 carbon atoms, and where $X^2$, $X^3$ are each selected independently, with the exclusion of: $X^2=X^3=$hydrogen;

where $Y^2$ is selected from the group consisting of unbranched or branched alkylene group having 1 to 30 carbon atoms, divalent saturated hydrocarbyl group having 3 to 30 carbon atoms and having at least one saturated ring composed of 3 to 30 carbon atoms, divalent hydrocarbyl group having 6 to 30 carbon atoms, of which at least 6 carbon atoms are present in an aromatic system and the other carbon atoms, if present, are saturated, a bridging radical having a chemical structure selected from the group consisting of (i), (ii) with

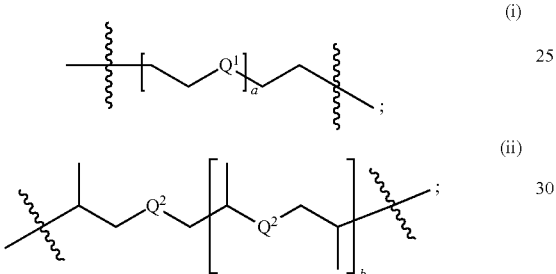

where $Q^1$, $Q^2$ are each independently selected from the group consisting of —O—, —S—, —NH— and —NR$^4$— with $R^4$=unbranched or branched alkyl group having 1 to 6 carbon atoms, where a is an integer selected from the range of 1 to 50, where b is an integer selected from the range of 0 to 50, and where $Y^2$ may also be a direct bond if at least one of $p^3$ and $p^4$ has the value of 1, and where $Z^4$ is selected from the group consisting of —O—, —S—, —NR$^{30}$—;

where the $R^{30}$ radical is selected from the group consisting of hydrogen, unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$), unbranched or branched acyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$);

a radical having a chemical structure selected from the group consisting of (iii), (iv), (v), (vi), (vii), (viii), (ix) with

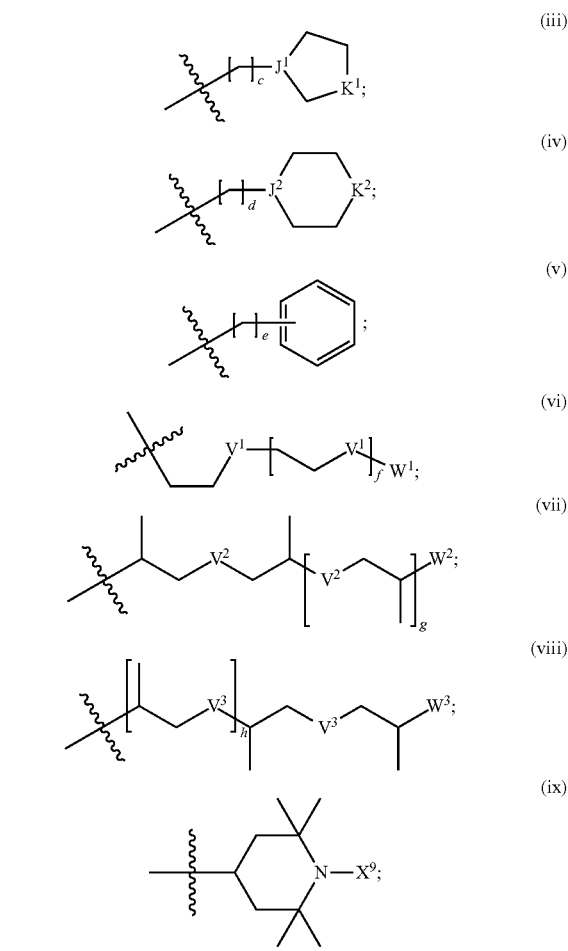

where $J^1$, $J^2$ are each independently selected from the group consisting of CH, N, where $K^1$, $K^2$ are each independently selected from the group consisting of —O—, —NH—, —N(CH$_3$)—, —N(CH$_2$CH$_3$)—, —S—, —CH$_2$—, where $V^1$, $V^2$, $V^3$ are each independently selected from the group consisting of —O—, —S—, —NH—, —NR"— with R"=unbranched or branched alkyl group having 1 to 6 carbon atoms, here $W^1$, $W^2$, $W^3$ are each independently selected from the group consisting of H, methyl, ethyl, where c, d, e, f, g, h are each independently an integer from the range of 0 to 50, where $X^9$ is selected from the group consisting of hydrogen, —OH, —O., unbranched or branched alkyl group having 1 to 10 carbon atoms, unbranched or branched alkoxy group having 1 to 10 carbon atoms, where, in the chemical structures (iii), (iv), (v), (vi), (vii), (viii), (ix), at least one hydrogen radical bonded to a carbon atom may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$), and wherein reductive conditions are established by reacting the at least one triacetonamine compound (I) with formaldehyde in the presence of hydrogen and in the presence of a supported catalyst, where the supported catalyst includes at least one metal M, where the metal M is selected from the group consisting of V, Cr, Mo, Mn, Ni, Pd, Pt, Fe, Ru, Os, Co, Rh, Ir, Cu.

6.2 Process according to Point 6.1, where $p^3=p^4=0$.

6.3 Process according to Point 6.1 or 6.2, where $Y^2$ is selected from the group consisting of
unbranched or branched alkylene group having 1 to 30 carbon atoms,
divalent saturated hydrocarbyl group having 3 to 30 carbon atoms and having at least one saturated ring composed of 3 to 30 carbon atoms.

6.4 Process according to one or more of Points 6.1 to 6.3, where the $R^{30}$ radical is selected from the group consisting of
hydrogen,
unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$),
a radical having a chemical structure (ix) with

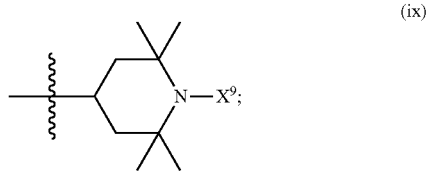

(ix)

where $X^9$ is selected from the group consisting of hydrogen, —OH, —O., unbranched or branched alkyl group having 1 to 10 carbon atoms, unbranched or branched alkoxy group having 1 to 10 carbon atoms.

6.5 Process according to one or more of Points 6.1 to 6.4, where the $R^{30}$ radical is selected from the group consisting of
hydrogen,
unbranched or branched alkyl group having 1 to 12 carbon atoms,
a radical having a chemical structure (ix) with

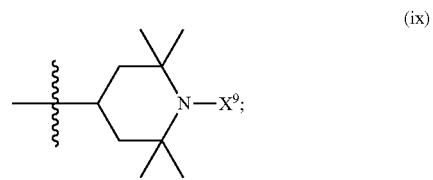

(ix)

where $X^9$ is selected from the group consisting of hydrogen, —OH, —O., unbranched or branched alkyl group having 1 to 10 carbon atoms, unbranched or branched alkoxy group having 1 to 10 carbon atoms.

6.6 Process according to one or more of Points 6.1 to 6.5, where the $R^{30}$ radical is selected from the group consisting of hydrogen, unbranched or branched alkyl group having 1 to 6 carbon atoms.

6.7 Process according to one or more of Points 6.1 to 6.6, where $X^9$=hydrogen.

6.8 Process according to one or more of Points 6.1 to 6.7, wherein formaldehyde is used as a gas, as an aqueous solution or as a solid, preferably as an aqueous solution or as a solid, more preferably as an aqueous solution.

6.9 Process according to one or more of Points 6.1 to 6.8, wherein the at least one triacetonamine compound (I) is reacted with formaldehyde under reductive conditions in at least one solvent, where the solvent is selected from the group consisting of aliphatic solvents, aromatic solvents, ethers, halogenated solvents, amides, thio compounds, carboxylic acids, alcohols, water.

6.10 Process according to one or more of Points 6.1 to 6.9, wherein the at least one triacetonamine compound (I) is reacted with formaldehyde under reductive conditions at a temperature in the range from 20° C. to 350° C. and a pressure in the range from 2 bar to 500 bar.

The present invention relates, in a seventh aspect, to a process according to the following Points 7.1 to 7.9.

7.1 Process for preparing an N-methyl-substituted triacetonamine compound,
characterized in that at least one triacetonamine compound (I) is reacted with formaldehyde under reductive conditions,
where the triacetonamine compound (I) has the chemical structure (I-F) with

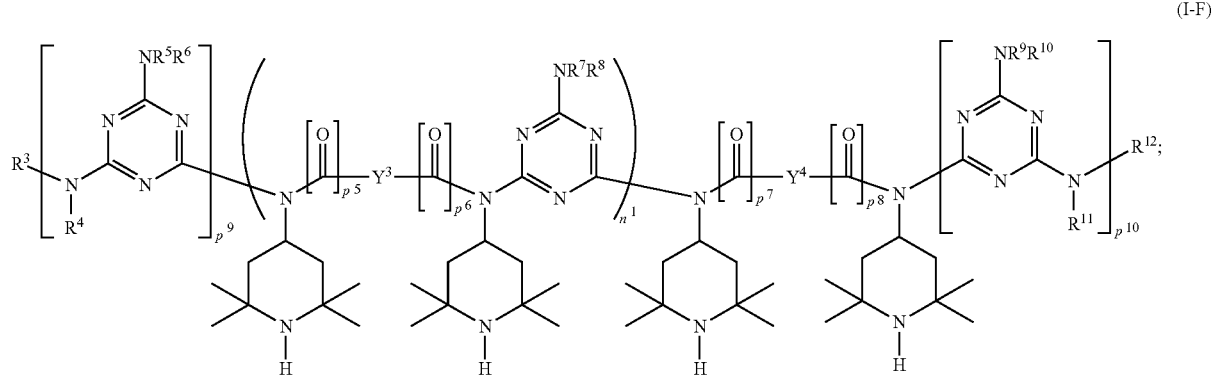

(I-F)

where $n^1$ is an integer from the range of 1 to 20;
where $p^5$, $p^6$, $p^7$, $p^8$, $p^9$, $p^{10}$ are each independently 0 or 1;
where $Y^3$, $Y^4$ are each independently selected from the group consisting of
  unbranched or branched alkylene group having 1 to 30 carbon atoms,
  divalent saturated hydrocarbyl group having 3 to 30 carbon atoms and having at least one saturated ring composed of 3 to 30 carbon atoms,
  divalent hydrocarbyl group having 6 to 30 carbon atoms, of which at least 6 carbon atoms are present in an aromatic system and the other carbon atoms, if present, are saturated,
  a bridging radical having a chemical structure selected from the group consisting of (i), (ii) with

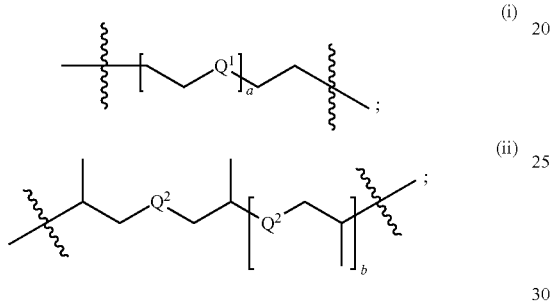

where
  $Q^1$, $Q^2$ are each independently selected from the group consisting of —O—, —S—, —NH— and —NR'— with R'=unbranched or branched alkyl group having 1 to 6 carbon atoms,
  where a is an integer selected from the range of 1 to 50,
  where b is an integer selected from the range of 0 to 50,
  and where $Y^3$ may also be a direct bond if at least one of $p^5$ and $p^6$ has the value of 1,
  and where $Y^4$ may also be a direct bond if at least one of $p^7$ and $p^8$ has the value of 1,
  where the $R^3$, $R^4$, $R^5$, $R^6$, $R^9$, $R^{10}$, $R^{11}$, $R^{12}$ radicals are each independently selected from the group consisting of
hydrogen,
  unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$),
  unbranched or branched acyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$);
  a radical having a chemical structure selected from the group consisting of (iii), (iv), (v), (vi), (vii), (viii), (ix) with

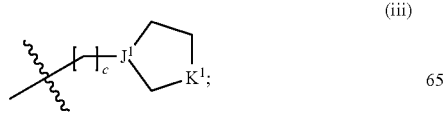

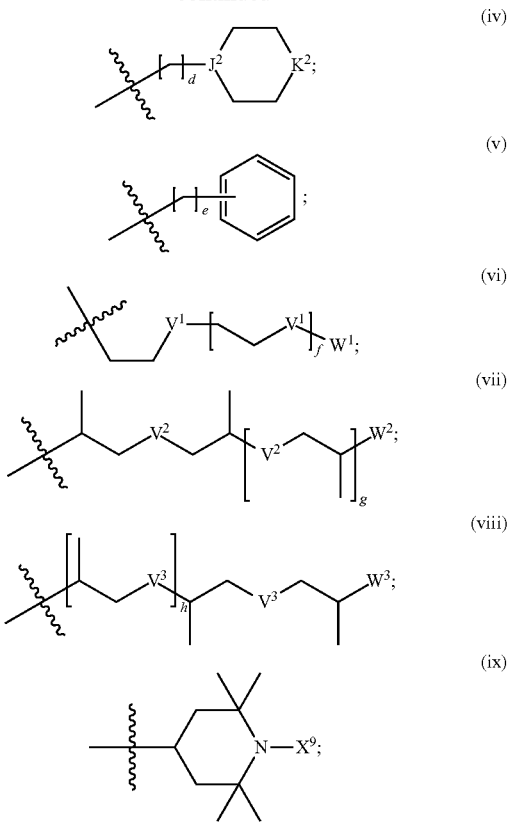

where $J^1$, $J^2$ are each independently selected from the group consisting of CH, N,
where $K^1$, $K^2$ are each independently selected from the group consisting of —O—, —NH—, —N(CH$_3$)—, —N(CH$_2$CH$_3$)—, —S—, —CH$_2$—,
where $V^1$, $V^2$, $V^3$ are each independently selected from the group consisting of —O—, —S—, —NH—, —NR"— with R"=unbranched or branched alkyl group having 1 to 6 carbon atoms,
where $W^1$, $W^2$, $W^3$ are each independently selected from the group consisting of H, methyl, ethyl,
where c, d, e, f, g, h are each independently an integer from the range of 0 to 50,
where $X^9$ is selected from the group consisting of hydrogen, —OH, —O., unbranched or branched alkyl group having 1 to 10 carbon atoms, unbranched or branched alkoxy group having 1 to 10 carbon atoms,
where, in the chemical structures (iii), (iv), (v), (vi), (vii), (viii), (ix), at least one hydrogen radical bonded to a carbon atom may be replaced by a radical selected from the group consisting of
—OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$);
where the $R^7$, $R^8$ radicals are each independently selected from the group consisting of
hydrogen,
  unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$),
unbranched or branched acyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$);

and where, when p$^9$=1, —NR$^3$R$^4$ may also be a radical of the chemical structure (x), and where, when p$^{10}$=1, —NR$^{11}$R$^{12}$ may also be a radical of the chemical structure (x), and where the —NR$^5$R$^6$, —NR$^7$R$^8$, —NR$^9$R$^{10}$ radicals may each independently also be a radical of the chemical structure (x), where the chemical structure (x) is defined as follows:

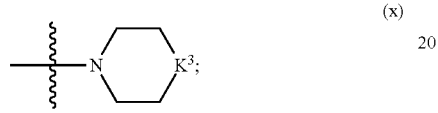

where K$^3$ is selected from the group consisting of —O—, —S—, —NH—, —N(CH$_3$)—, —N(CH$_2$CH$_3$)—, where K$^3$ is preferably —O—, and wherein reductive conditions are established by reacting the at least one triacetonamine compound (I) with formaldehyde in the presence of hydrogen and in the presence of a supported catalyst, where the supported catalyst includes at least one metal M, where the metal M is selected from the group consisting of V, Cr, Mo, Mn, Ni, Pd, Pt, Fe, Ru, Os, Co, Rh, Ir, Cu.

7.2 Process according to Point 7.1, where p$^5$=p$^6$=p$^7$=p$^8$=0 and where p$^9$, p$^{10}$ are each independently 0 or 1; preferably, p$^5$=p$^6$=p$^7$=p$^8$=0 and at least one of p$^9$, p$^{10}$ is 1 (where, logically, if only one of p$^9$, p$^{10}$=1, the other of p$^9$, p$^{10}$=0); even more preferably, p$^5$=p$^6$=p$^7$=p$^8$=0 and p$^9$=p$^{10}$=1.

7.3 Process according to Point 7.1 or 7.2, where Y$^3$, Y$^4$ are each independently selected from the group consisting of
unbranched or branched alkylene group having 1 to 30 carbon atoms,
divalent saturated hydrocarbyl group having 3 to 30 carbon atoms and having at least one saturated ring composed of 3 to 30 carbon atoms.

7.4 Process according to one or more of Points 7.1 to 7.3, where the R$^3$, R$^4$, R$^5$, R$^6$, R$^9$, R$^{10}$, R$^{11}$, R$^{12}$ radicals are each independently selected from the group consisting of
hydrogen,
unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$),
a radical having a chemical structure (ix) with

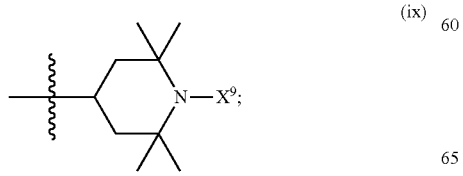

where X$^9$ is selected from the group consisting of hydrogen, —OH, —O., unbranched or branched alkyl group having 1 to 10 carbon atoms, unbranched or branched alkoxy group having 1 to 10 carbon atoms;

where the R$^7$, R$^8$ radicals are each independently selected from the group consisting of
hydrogen,
unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$), and where, when p$^9$=1, —NR$^3$R$^4$ may also be a radical of the chemical structure (x), and where, when p$^{10}$=1, —NR$^{11}$R$^{12}$ may also be a radical of the chemical structure (x), and where the —NR$^5$R$^6$, —NR$^7$R$^8$, —NR$^9$R$^{10}$ radicals may each independently also be a radical of the chemical structure (x), where the chemical structure (x) is defined as follows:

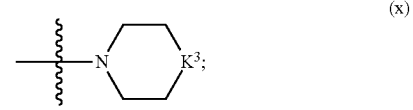

where K$^3$ is selected from the group consisting of —O—, —S—, —NH—, —N(CH$_3$)—, —N(CH$_2$CH$_3$)—, where K$^3$ is preferably —O—.

7.5 Process according to one or more of Points 7.1 to 7.4, where the R$^3$, R$^4$, R$^5$, R$^6$, R$^9$, R$^{10}$, R$^{11}$, R$^{12}$ radicals are each independently selected from the group consisting of
hydrogen,
unbranched or branched alkyl group having 1 to 12 carbon atoms,
a radical having a chemical structure (ix) with

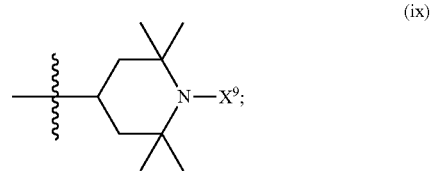

where X$^9$ is selected from the group consisting of hydrogen, —OH, —O., unbranched or branched alkyl group having 1 to 10 carbon atoms, unbranched or branched alkoxy group having 1 to 10 carbon atoms;

where the R$^7$, R$^8$ radicals are each independently selected from the group consisting of
hydrogen,
unbranched or branched alkyl group having 1 to 12 and preferably 1 to 6 carbon atoms,
and where the —NR$^7$R$^8$ radical may also be a radical of the chemical structure (x) with

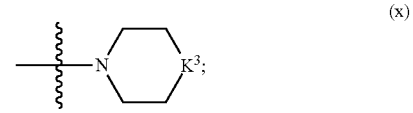

where K$^3$=—O—.

7.6 Process according to one or more of Points 7.1 to 7.5, where X⁹=hydrogen.

7.7 Process according to one or more of Points 7.1 to 7.6, wherein formaldehyde is used as a gas, as an aqueous solution or as a solid, preferably as an aqueous solution or as a solid, more preferably as an aqueous solution.

7.8 Process according to one or more of Points 7.1 to 7.7, wherein the at least one triacetonamine compound (I) is reacted with formaldehyde under reductive conditions in at least one solvent, where the solvent is selected from the group consisting of aliphatic solvents, aromatic solvents, ethers, halogenated solvents, amides, thio compounds, carboxylic acids, alcohols, water.

7.9 Process according to one or more of Points 7.1 to 7.8, wherein the at least one triacetonamine compound (I) is reacted with formaldehyde under reductive conditions at a temperature in the range from 20° C. to 350° C. and a pressure in the range from 2 bar to 500 bar.

The present invention relates, in an eighth aspect, to a process according to the following Points 8.1 to 8.9.

8.1 Process for preparing an N-methyl-substituted triacetonamine compound,
characterized in that at least one triacetonamine compound (I) is reacted with formaldehyde under reductive conditions,
where the triacetonamine compound (I) has the chemical structures (I-G) with divalent hydrocarbyl group having 6 to 30 carbon atoms, of which at least 6 carbon atoms are present in an aromatic system and the other carbon atoms, if present, are saturated, a bridging radical having a chemical structure selected from the group consisting of (i), (ii) with

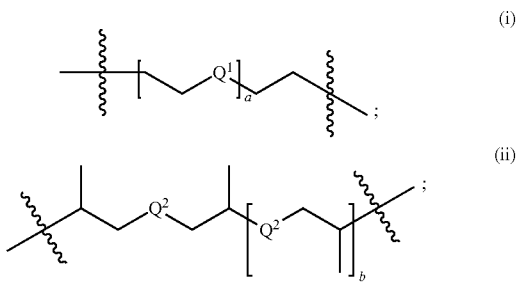

where
$Q^1$, $Q^2$ are each independently selected from the group consisting of —O—, —S—, —NH— and —NR'— with R'=unbranched or branched alkyl group having 1 to 6 carbon atoms, where a is an integer selected from the range of 1 to 50, where b is an integer selected from the range of 0 to 50,

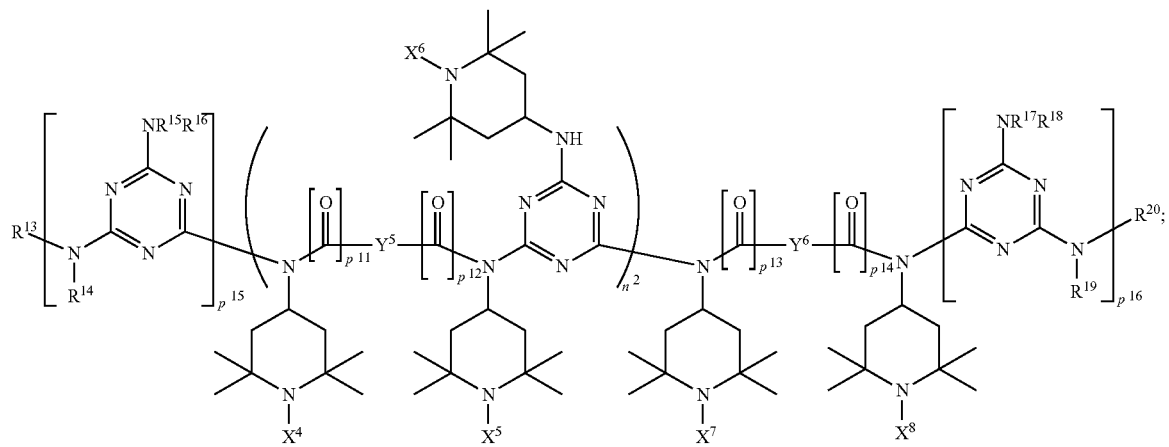

(I-G)

where $n^2$ is an integer from the range of 1 to 20;

where $p^{11}$, $p^{12}$, $p^{13}$, $p^{14}$, $p^{15}$, $p^{16}$ are each independently 0 or 1;

where $X^4$, $X^5$, $X^6$, $X^7$, $X^8$ are each independently selected from the group consisting of hydrogen, OH, —O., unbranched or branched alkyl group having 1 to 10 carbon atoms, unbranched or branched alkoxy group having 1 to 10 carbon atoms;

where $Y^5$, $Y^6$ are each independently selected from the group consisting of
unbranched or branched alkylene group having 1 to 30 carbon atoms,
divalent saturated hydrocarbyl group having 3 to 30 carbon atoms and having at least one saturated ring composed of 3 to 30 carbon atoms, and where $Y^5$ may also be a direct bond if at least one of $p^{11}$ and $p^{12}$ has the value of 1, and where $Y^6$ may also be a direct bond if at least one of $p^{13}$ and $p^{14}$ has the value of 1;

where the $R^{13}$, $R^{14}$, $R^{15}$, $R^{16}$, $R^{17}$, $R^{18}$, $R^{19}$, $R^{20}$ radicals are each independently selected from the group consisting of
hydrogen,
unbranched or branched alkyl group which has 1 to 30 carbon atoms and in which at least one hydrogen radical may be replaced by a radical selected from the group consisting of —OH, —NH₂, —OCH₃, —OCH₂CH₃, —NH(CH₃), —N(CH₃)₂, —NH(CH₂CH₃), —N(CH₂CH₃)₂, —N(CH₃)(CH₂CH₃),
unbranched or branched acyl group which has 1 to 30 carbon atoms and in which at least one hydrogen radical may be replaced by a radical selected from the group consisting of —OH, —NH₂, —OCH₃, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$);

a radical having a chemical structure selected from the group consisting of (iii), (iv), (v), (vi), (vii), (viii), (ix) with

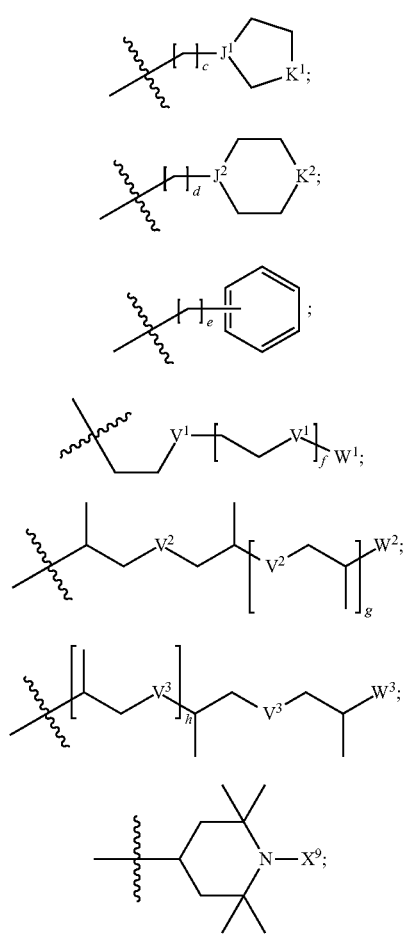

where J$^1$, J$^2$ are each independently selected from the group consisting of CH, N, where K$^1$, K$^2$ are each independently selected from the group consisting of —O—, —NH—, —N(CH$_3$)—, —N(CH$_2$CH$_3$)—, —S—, —CH$_2$—, where V$^1$, V$^2$, V$^3$ are each independently selected from the group consisting of —O—, —S—, —NH—, —NR″— with R″=unbranched or branched alkyl group having 1 to 6 carbon atoms, where W$^1$, W$^2$, W$^3$ are each independently selected from the group consisting of H, methyl, ethyl, where c, d, e, f, g, h are each independently an integer from the range of 0 to 50, where X$^9$ is selected from the group consisting of hydrogen, —OH, —O., unbranched or branched alkyl group having 1 to 10 carbon atoms, unbranched or branched alkoxy group having 1 to 10 carbon atoms, where, in the chemical structures (iii), (iv), (v), (vi), (vii), (viii), (ix), at least one hydrogen radical bonded to a carbon atom may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$), and wherein reductive conditions are established by reacting the at least one triacetonamine compound (I) with formaldehyde in the presence of hydrogen and in the presence of a supported catalyst, where the supported catalyst includes at least one metal M, where the metal M is selected from the group consisting of V, Cr, Mo, Mn, Ni, Pd, Pt, Fe, Ru, Os, Co, Rh, Ir, Cu.

8.2 Process according to Point 8.1, where $p^{11}=p^{12}=p^{13}=p^{14}=0$ and where $p^{15}$, $p^{16}$ are each independently 0 or 1.

8.3 Process according to Point 8.1 or 8.2, where

Y$^5$, Y$^6$ are each independently selected from the group consisting of unbranched or branched alkylene group having 1 to 30 carbon atoms, divalent saturated hydrocarbyl group having 3 to 30 carbon atoms and having at least one saturated ring composed of 3 to 30 carbon atoms.

8.4 Process according to one or more of Points 8.1 to 8.3, where the R$^{13}$, R$^{14}$, R$^{15}$, R$^{16}$, R$^{17}$, R$^{18}$, R$^{19}$, R$^{20}$ radicals are each independently selected from the group consisting of hydrogen, unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$), a radical having a chemical structure (ix) with

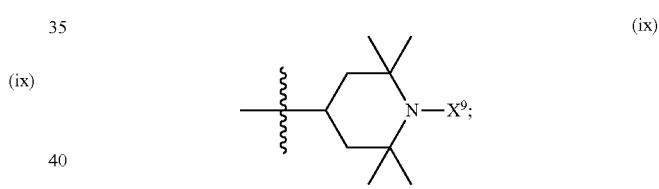

where X$^9$ is selected from the group consisting of hydrogen, —OH, —O., unbranched or branched alkyl group having 1 to 10 carbon atoms, unbranched or branched alkoxy group having 1 to 10 carbon atoms.

8.5 Process according to one or more of Points 8.1 to 8.4, where the R$^{13}$, R$^{14}$, R$^{15}$, R$^{16}$, R$^{17}$, R$^{18}$, R$^{19}$, R$^{20}$ radicals are each independently selected from the group consisting of hydrogen, unbranched or branched alkyl group having 1 to 12 and preferably 1 to 6 carbon atoms, a radical having a chemical structure (ix) with

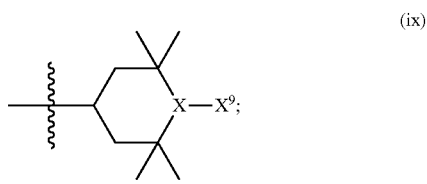

where X$^9$ is selected from the group consisting of hydrogen, —OH, —O., unbranched or branched alkyl group having 1 to 10 carbon atoms, unbranched or branched alkoxy group having 1 to 10 carbon atoms.

8.6 Process according to one or more of Points 8.1 to 8.5, where $X^4=X^5=X^6=X^7=X^8=X^9$=hydrogen.

8.7 Process according to one or more of Points 8.1 to 8.6, wherein formaldehyde is used as a gas, as an aqueous solution or as a solid, preferably as an aqueous solution or as a solid, more preferably as an aqueous solution.

8.8 Process according to one or more of Points 8.1 to 8.7, wherein the at least one triacetonamine compound (I) is reacted with formaldehyde under reductive conditions in at least one solvent, where the solvent is selected from the group consisting of aliphatic solvents, aromatic solvents, ethers, halogenated solvents, amides, thio compounds, carboxylic acids, alcohols, water.

8.9 Process according to one or more of Points 8.1 to 8.8, wherein the at least one triacetonamine compound (I) is reacted with formaldehyde under reductive conditions at a temperature in the range from 20° C. to 350° C. and a pressure in the range from 2 bar to 500 bar.

The present invention relates, in a ninth aspect, to a process according to the following Points 9.1 to 9.8.

9.1 Process for preparing an N-methyl-substituted triacetonamine compound, characterized in that at least one triacetonamine compound (I) is reacted with formaldehyde under reductive conditions, where the triacetonamine compound (I) has the chemical structures (I-H) with

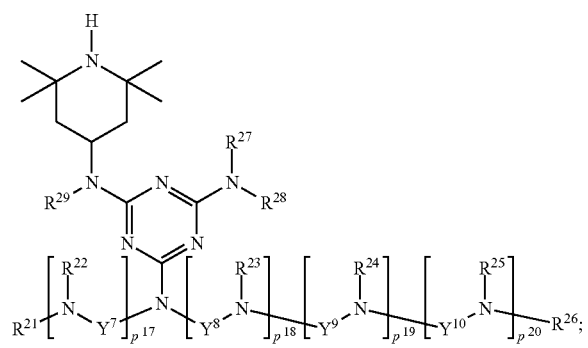

(I-H)

where $p^{17}$, $p^{18}$, $p^{19}$, $p^{20}$ are each independently 0 or 1;

where $Y^7$, $Y^8$, $Y^9$, $Y^{10}$ are each independently selected from the group consisting of unbranched or branched alkylene group having 1 to 30 carbon atoms, divalent saturated hydrocarbyl group having 3 to 30 carbon atoms and having at least one saturated ring composed of 3 to 30 carbon atoms, divalent hydrocarbyl group having 6 to 30 carbon atoms, of which at least 6 carbon atoms are present in an aromatic system and the other carbon atoms, if present, are saturated, a bridging radical having a chemical structure selected from the group consisting of (i), (ii) with

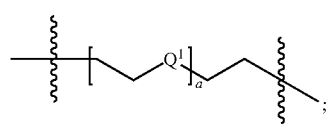

(i)

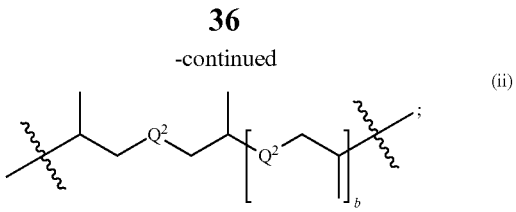

(ii)

where $Q^1$, $Q^2$ are each independently selected from the group consisting of —O—, —S—, —NH— and —NR'— with R'=unbranched or branched alkyl group having 1 to 6 carbon atoms, where a is an integer selected from the range of 1 to 50, where b is an integer selected from the range of 0 to 50, where the $R^{21}$, $R^{22}$, $R^{23}$, $R^{24}$, $R^{25}$, $R^{26}$ radicals are each independently selected from the group consisting of hydrogen, unbranched or branched alkyl group having 1 to 30 carbon atoms, a group having the chemical structure (xi) with

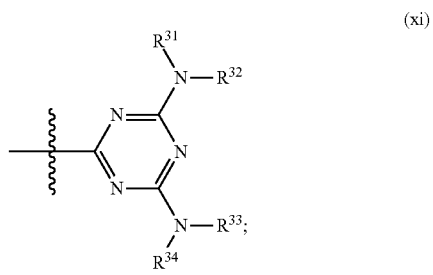

(xi)

where the $R^{27}$, $R^{28}$, $R^{29}$, $R^{31}$, $R^{32}$, $R^{33}$, $R^{34}$ radicals are each independently selected from the group consisting of hydrogen, unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$), unbranched or branched acyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$);

a radical having a chemical structure selected from the group consisting of (xii), (xiii), (xiv), (xv), (xvi), (xvii), (xviii) with

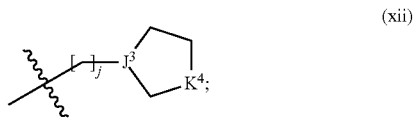

(xii)

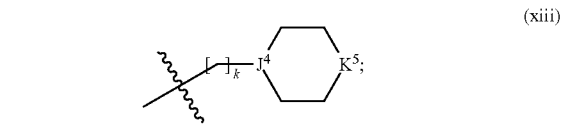

(xiii)

-continued

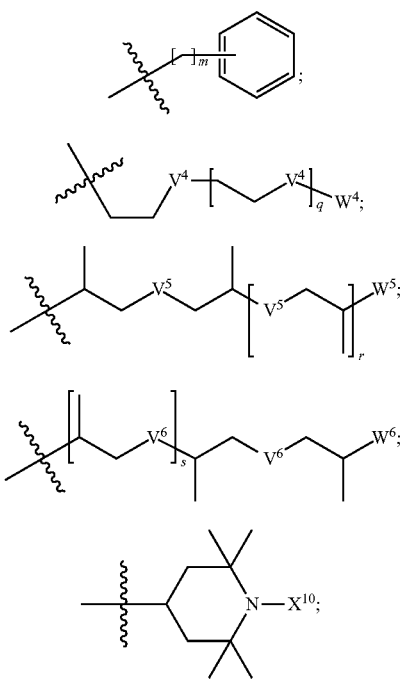

(xiv)

(xv)

(xvi)

(xvii)

(xviii)

where $J^3$, $J^4$ are each independently selected from the group consisting of CH, N,
where $K^4$, $K^5$ are each independently selected from the group consisting of —O—, —NH—, —N(CH$_3$)—, —N(CH$_2$CH$_3$)—, —S—, —CH$_2$—,
where $V^4$, $V^5$, $V^6$ are each independently selected from the group consisting of —O—, —S—, —NH—, —NR'''— with R'''=unbranched or branched alkyl group having 1 to 6 carbon atoms,
where $W^4$, $W^5$, $W^6$ are each independently selected from the group consisting of H, methyl, ethyl,
where j, k, m, q, r, s are each independently an integer from the range of 0 to 50,
where $X^{10}$ is selected from the group consisting of hydrogen, —OH, —O., unbranched or branched alkyl group having 1 to 10 carbon atoms, unbranched or branched alkoxy group having 1 to 10 carbon atoms,
where, in the chemical structures (xii), (xiii), (xiv), (xv), (xvi), (xvii), (xviii), at least one hydrogen radical bonded to a carbon atom may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$),
and with the proviso that $R^{21}$ and $R^{26}$, when $p^{17}=p^{18}=p^{19}=p^{20}=0$, may each independently also be a group of the chemical structure (xix) with

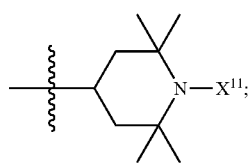

(xix)

where $X^{11}$ is selected from the group consisting of hydrogen, OH, —O., unbranched or branched alkyl group having 1 to 10 carbon atoms, unbranched or branched alkoxy group having 1 to 10 carbon atoms,
and wherein reductive conditions are established by reacting the at least one triacetonamine compound (I) with formaldehyde in the presence of hydrogen and in the presence of a supported catalyst, where the supported catalyst includes at least one metal M, where the metal M is selected from the group consisting of V, Cr, Mo, Mn, Ni, Pd, Pt, Fe, Ru, Os, Co, Rh, Ir, Cu.

9.2 Process according to Point 9.1, where
$Y^7$, $Y^8$, $Y^9$, $Y^{10}$ are each independently selected from the group consisting of unbranched or branched alkylene group having 1 to 30 carbon atoms,
divalent saturated hydrocarbyl group having 3 to 30 carbon atoms and having
at least one saturated ring composed of 3 to 30 carbon atoms.

9.3 Process according to one or more of Points 9.1 to 9.2, where the $R^{21}$, $R^{22}$, $R^{23}$, $R^{24}$, $R^{25}$, $R^{26}$ radicals are each independently selected from the group consisting of
hydrogen,
unbranched or branched alkyl group having 1 to 30 carbon atoms,
a group having the chemical structure (xi) with

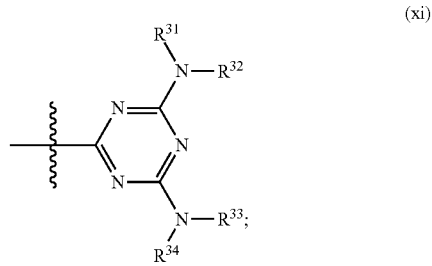

(xi)

where the $R^{27}$, $R^{28}$, $R^{29}$, $R^{31}$, $R^{32}$, $R^{33}$, $R^{34}$ radicals are each independently selected from the group consisting of
hydrogen,
unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$),
a radical having a chemical structure (xvii) with

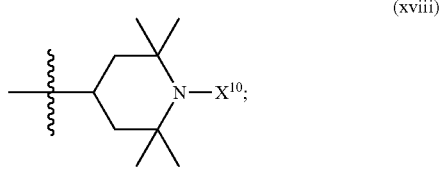

(xviii)

where $X^{10}$ is selected from the group consisting of hydrogen, OH, —O.,
unbranched or branched alkyl group having 1 to 10 carbon atoms, unbranched or branched alkoxy group having 1 to 10 carbon atoms,
and with the proviso that $R^{21}$ and $R^{26}$, when $p^{17}=p^{18}=p^{19}=p^{20}=0$, may each independently also be a group of the chemical structure (xix) with

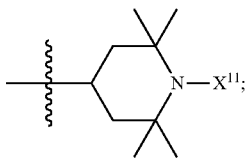

where $X^{11}$ is selected from the group consisting of hydrogen, —OH, —O., unbranched or branched alkyl group having 1 to 10 carbon atoms, unbranched or branched alkoxy group having 1 to 10 carbon atoms.

9.4 Process according to one or more of Points 9.1 to 9.3, where the $R^{21}$, $R^{22}$, $R^{23}$, $R^{24}$, $R^{25}$, $R^{26}$ radicals are each independently selected from the group consisting of hydrogen, unbranched or branched alkyl group having 1 to 12 and preferably 1 to 6 carbon atoms, a group having the chemical structure (xi) with

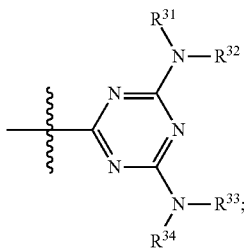

where the $R^{27}$, $R^{28}$, $R^{29}$, $R^{31}$, $R^{32}$, $R^{33}$, $R^{34}$ radicals are each independently selected from the group consisting of hydrogen, unbranched or branched alkyl group having 1 to 12 and preferably 1 to 6 carbon atoms, a radical having a chemical structure (xviii) with

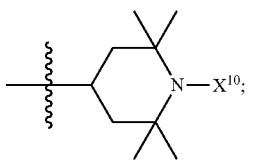

where $X^{10}$ is selected from the group consisting of hydrogen, —OH, —O., unbranched or branched alkyl group having 1 to 10 carbon atoms, unbranched or branched alkoxy group having 1 to 10 carbon atoms, and with the proviso that $R^{21}$ and $R^{26}$, when $p^{17}=p^{18}=p^{19}=p^{20}=0$, may each independently also be a group of the chemical structure (xix) with

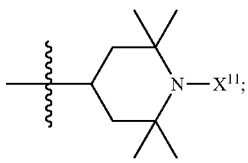

where $X^{11}$ is selected from the group consisting of hydrogen, OH, —O., unbranched or branched alkyl group having 1 to 10 carbon atoms, unbranched or branched alkoxy group having 1 to 10 carbon atoms.

9.5 Process according to one or more of Points 9.1 to 9.4, where $X^9=X^{10}=X^{11}$=hydrogen.

9.6 Process according to one or more of Points 9.1 to 9.5, wherein formaldehyde is used as a gas, as an aqueous solution or as a solid, preferably as an aqueous solution or as a solid, more preferably as an aqueous solution.

9.7 Process according to one or more of Points 9.1 to 9.6, wherein the at least one triacetonamine compound (I) is reacted with formaldehyde under reductive conditions in at least one solvent, where the solvent is selected from the group consisting of aliphatic solvents, aromatic solvents, ethers, halogenated solvents, amides, thio compounds, carboxylic acids, alcohols, water.

9.8 Process according to one or more of Points 9.1 to 9.7, wherein the at least one triacetonamine compound (I) is reacted with formaldehyde under reductive conditions at a temperature in the range from 20° C. to 350° C. and a pressure in the range from 2 bar to 500 bar.

GENERAL TERMS

In the context of the invention, an "unbranched or branched alkyl group" is a monovalent saturated hydrocarbyl radical of the general chemical structure (a) with

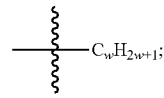

The chain of carbon atoms "—$C_wH_{2w+1}$" may be linear, in which case the group is an unbranched alkyl group. Alternatively, it may have branches, in which case it is a branched alkyl group.

w in the chemical structure (a) is an integer. w in an unbranched or branched alkyl group having 1 to 30 carbon atoms is selected from the range of 1 to 30. w in an unbranched or branched alkyl group having 1 to 29 carbon atoms is selected from the range of 1 to 29. w in an unbranched or branched alkyl group having 1 to 12 carbon atoms is selected from the range of 1 to 12. w in an unbranched or branched alkyl group having 1 to 10 carbon atoms is selected from the range of 1 to 10. w in an unbranched or branched alkyl group having 1 to 8 carbon atoms is selected from the range of 1 to 8. w in an unbranched or branched alkyl group having 1 to 6 carbon atoms is selected from the range of 1 to 6.

In the context of the invention, an "unbranched or branched alkyl group having 1 to 30 carbon atoms" is especially selected from methyl, ethyl, n-propyl, iso-propyl, n-butyl, sec-butyl, iso-butyl, tert-butyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-eicosyl, n-heneicosyl, n-docosyl, n-tricosyl, n-tetracosyl, n-pentacosyl, n-hexacosyl, n-heptacosyl, n-octacosyl, n-nonacosyl, n-triacontyl.

In the context of the invention, an "unbranched or branched alkyl group having 1 to 12 carbon atoms" is especially selected from the group consisting of methyl, ethyl, n-propyl, iso-propyl, n-butyl, sec-butyl, iso-butyl, tert-butyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl, n-decyl, n-undecyl, n-dodecyl.

In the context of the invention, an "unbranched or branched alkyl group having 1 to 10 carbon atoms" is especially selected from the group consisting of methyl, ethyl, n-propyl, iso-propyl, n-butyl, sec-butyl, iso-butyl, tert-butyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl, n-decyl.

In the context of the invention, an "unbranched or branched alkyl group having 1 to 8 carbon atoms" is especially selected from the group consisting of methyl, ethyl, n-propyl, iso-propyl, n-butyl, sec-butyl, iso-butyl, tert-butyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl.

In the context of the invention, an "unbranched or branched alkyl group having 1 to 6 carbon atoms" is especially selected from the group consisting of methyl, ethyl, n-propyl, iso-propyl, n-butyl, sec-butyl, iso-butyl, tert-butyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl.

The term "unbranched or branched alkylene group" in the context of the invention denotes a divalent saturated hydrocarbyl radical which can be described by the general chemical structure (b) with

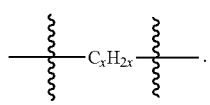

(b)

The chain of carbon atoms "—$C_xH_{2x}$—" may be linear, in which case the group is an unbranched alkylene group. Alternatively, it may have branches, in which case it is a branched alkylene group. x in the chemical structure (b) is an integer.

x in an unbranched or branched alkylene group having 1 to 30 carbon atoms is selected from the range of 1 to 30.

x in an unbranched or branched alkylene group having 1 to 12 carbon atoms is selected from the range of 1 to 12.

x in an unbranched or branched alkylene group having 1 to 6 carbon atoms is selected from the range of 1 to 6.

In the context of the invention, a "divalent saturated hydrocarbyl group having 3 to 30 carbon atoms and having at least one saturated ring composed of 3 to 30 carbon atoms" is especially a chemical structure (c) with

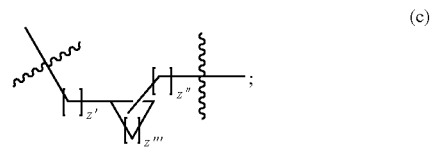

(c)

where $z'$ is an integer from 0 to 27; where $z''$ is an integer from 0 to 27; where $z'''$ is an integer from 1 to 28; and where, at the same time, $z'+z''+z''' \leq 28$.

More particularly, a "divalent saturated hydrocarbyl group having 3 to 30 carbon atoms and having at least one saturated ring composed of 3 to 30 carbon atoms" is a "divalent saturated hydrocarbyl group having 3 to 12 carbon atoms and having at least one saturated ring composed of 3 to 12 carbon atoms", more preferably "divalent saturated hydrocarbyl group having 3 to 6 carbon atoms and having at least one saturated ring composed of 3 to 6 carbon atoms".

A "divalent saturated hydrocarbyl group having 3 to 12 carbon atoms and having at least one saturated ring composed of 3 to 12 carbon atoms" in the context of the invention has a chemical structure (c) where $z'$ is an integer from 0 to 9; where $z''$ is an integer from 0 to 9; where $z'''$ is an integer from 1 to 10; and where, at the same time, $z'+z''+z''' \leq 10$.

Preferably, a "divalent saturated hydrocarbyl group having 3 to 12 carbon atoms and having at least one saturated ring composed of 3 to 12 carbon atoms" is selected from the group consisting of cyclopropylene, cyclobutylene, cyclopentylene, cyclohexylene, cycloheptylene, cyclooctylene, cyclononylene, cyclodecylene, cycloundecylene, cyclododecylene.

A "divalent saturated hydrocarbyl group having 3 to 6 carbon atoms and having at least one saturated ring composed of 3 to 6 carbon atoms" in the context of the invention has a chemical structure (c) where $z'$ is an integer from 0 to 3; where $z''$ is an integer from 0 to 3; where $z'''$ is an integer from 1 to 4; and where, at the same time, $z'+z''+z''' \leq 4$.

Preferably, a "divalent saturated hydrocarbyl group having 3 to 6 carbon atoms and having at least one saturated ring composed of 3 to 6 carbon atoms" is selected from the group consisting of cyclopropylene, cyclobutylene, cyclopentylene, cyclohexylene.

In the context of the invention, a "divalent hydrocarbyl group having 6 to 30 carbon atoms, of which at least 6 carbon atoms are present in an aromatic system and the other carbon atoms, if present, are saturated" is especially a "divalent hydrocarbyl group having 6 to 30 carbon atoms, of which 6, 10 or 14 carbon atoms are present in an aromatic system and the other carbon atoms, if present, are saturated", and is more preferably selected from the group consisting of naphthylene, anthrylene, phenanthrylene and the following chemical structure (d):

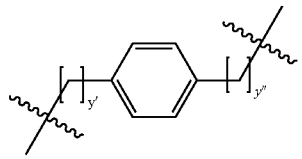

(d)

where y' is an integer from 0 to 24; where y" is an integer from 0 to 24; and where, at the same time, y'+y"≤24.

Even more preferably, it is a "divalent hydrocarbyl group having 6 to 30 carbon atoms, of which 6 or 10 carbon atoms are present in an aromatic system and the other carbon atoms, if present, are saturated", and this group is then most preferably selected from the group consisting of naphthylene and the following chemical structure (d):

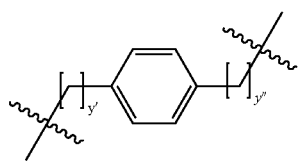

(d)

where y' is an integer from 0 to 24; where y" is an integer from 0 to 24; and where, at the same time, y'+y"≤24.

In the context of the invention, an "unbranched or branched alkoxy group" is an organic radical of the chemical structure

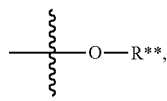

in which R is an unbranched or branched alkyl group. In an "unbranched or branched alkoxy group having 1 to 30 carbon atoms", R is an unbranched or branched alkyl group having 1 to 30 carbon atoms.

In an "unbranched or branched alkoxy group having 1 to 10 carbon atoms", R** is an unbranched or branched alkyl group having 1 to 10 carbon atoms.

In the context of the invention, an "unbranched or branched alkoxy group having 1 to 10 carbon atoms" is especially selected from the group consisting of methoxy, ethoxy, n-propoxy, iso-propoxy, n-butoxy, sec-butoxy, iso-butoxy, tert-butoxy, n-pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy, n-heptoxy, n-octoxy, n-nonoxy, n-decoxy.

In the context of the invention, an "unbranched or branched acyl group having 1 to 30 carbon atoms" is an organic radical of the chemical structure

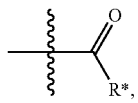

in which R* is an unbranched or branched alkyl radical having 1 to 29 carbon atoms.

More particularly, R* is selected from the group consisting of methyl, ethyl, n-propyl, iso-propyl, n-butyl, sec-butyl, iso-butyl, tert-butyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-eicosyl, n-heneicosyl, n-docosyl, n-tricosyl, n-tetracosyl, n-pentacosyl, n-hexacosyl, n-heptacosyl, n-octacosyl, n-nonacosyl.

"—O." in the context of the invention denotes an oxygen-centred free-radical.

In the context of the invention, the wording "at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$)" means that the group in question is in unsubstituted form or, in the group in question, at least one hydrogen radical bonded to a carbon atom, preferably 1 to 5, more preferably 1 to 3 and most preferably 1 to 2 hydrogen radical(s) bonded to the same or different carbon atom(s), is/are replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, —N(CH$_3$)(CH$_2$CH$_3$).

Process According to the Invention

Formaldehyde is used in the process according to the invention in particular as a gas, as an aqueous solution or as a solid. Preference is given to using formaldehyde in the process according to the invention as an aqueous solution or as a solid (for example as paraformaldehyde).

In the even more preferred embodiment in which formaldehyde is used as an aqueous solution, the concentration of the formaldehyde in the solution is 1.0% to 37% by weight (w/w, "%" relates to the weight of the formaldehyde based on the total weight of aqueous solution). In the case of 37% by weight of formaldehyde, for example, 100 g of aqueous solution contain 37 g of formaldehyde.

The process according to the invention is conducted under reductive conditions. "Reductive conditions" are understood to mean the conditions under which the imine shown in the reaction scheme <1> is converted to the corresponding amine by addition of hydrogen.

In the process according to the invention, reductive conditions are established by reacting the at least one triacetonediamine compound (I) with the at least one carbonyl compound (II) in the presence of hydrogen and in the presence of a supported catalyst, where the supported catalyst includes at least one metal M, where the metal M is selected from the group consisting of V, Cr, Mo, Mn, Ni, Pd, Pt, Fe, Ru, Os, Co, Rh, Ir, Cu; preferably selected from the group consisting of V, Cr, Mo, Mn, Ni, Pd, Pt, Fe, Ru, Os, Co, Rh, Ir, Cu; more preferably selected from the group consisting of Cr, Mo, Mn, Ni, Pd, Pt, Ru, Rh; even more preferably selected from the group consisting of Cr, Ni, Pd, Pt; most preferably selected from the group consisting of Ni, Pd.

The use of a supported catalyst including at least one metal M is essential to the process according to the invention: such supported catalysts are known to those skilled in the art and are described particularly in EP 0 302 020 A2.

"Supported catalyst including at least one metal M" means more particularly that the metal M, which is preferably in the elemental state, has been applied to a support known to those skilled in the art, which may, for example, especially be selected from the group consisting of activated carbon, calcium carbonate, aluminium oxide, titanium dioxide, especially from the group consisting of aluminium oxide, activated carbon.

The proportion of metal M in the supported catalyst is not particularly restricted and is especially in the range of 0.1% to 30% by weight, preferably 1% to 10% by weight, more preferably 5% by weight. In this context, % by weight means the total weight of all the metals M encompassed by the particular supported catalyst, based on the total weight of the support encompassed by the particular supported catalyst.

Without such a supported catalyst, only unwanted products would be obtained. C. Harries describes, for example, on pages 220 to 222 of his article "Untersuchungen über die cyclischen Acetonbasen" [Studies of the Cyclic Acetone Bases] in Justus Liebigs Annalen der Chemie, volume 417, 1918, pages 107 to 191, a reaction of 4-amino-2,2,6,6-tetramethylaminopiperidine with acetic anhydride without a supported catalyst, which leads to high yields of the corresponding amide compound which is unwanted here.

The process according to the invention can be conducted without solvent or else in at least one solvent, preferably in at least one solvent. Suitable solvents are all solvents in which the reactants have good solubility and which also do not have any disruptive influence on the process according to the invention. More particularly, the solvent is selected from the group consisting of aliphatic solvents, aromatic solvents, ethers, halogenated solvents, amides, thio compounds, carboxylic acids, alcohols, water; preferably, the solvent is selected from the group consisting of aliphatic solvents, aromatic solvents, ethers, alcohols, water; more preferably, the solvent is selected from the group consisting of aliphatic solvents, aromatic solvents, ethers, alcohols, water; even more preferably, the solvent is selected from the group consisting of aliphatic solvents, aromatic solvents, alcohols, water. The solvent is more preferably selected from aromatic solvents (especially toluene), alcohols (especially methanol).

Aliphatic solvents are especially selected from the group consisting of pentane, hexane, heptane, octane, decane, cyclopentane, cyclohexane, methylcyclohexane, petroleum ether.

Aromatic solvents are especially selected from the group consisting of benzene, toluene, xylene, ethylbenzene, cumene, bromobenzene, chlorobenzene, dichlorobenzene, furan, preferably toluene.

Ethers are especially selected from the group consisting of diethyl ether, dipropyl ether, dibutyl ether, methyl tert-butyl ether, ethylene glycol monomethyl ether, ethylene glycol monoethyl ether, ethylene glycol dimethyl ether, ethylene glycol diethyl ether, diethylene glycol monomethyl ether, diethylene glycol monoethyl ether, diethylene glycol dimethyl ether, diethylene glycol diethyl ether, triethylene glycol monomethyl ether, triethylene glycol monoethyl ether, triethylene glycol dimethyl ether, triethylene glycol diethyl ether, polyethylene glycol monomethyl ether, polyethylene glycol monoethyl ether, polyethylene glycol dimethyl ether, polyethylene glycol diethyl ether, 1,4-dioxane, 1,3-dioxane, tetrahydrofuran.

Halogenated solvents are especially selected from the group consisting of dichloromethane, chloroform, tetrachloromethane.

Amides are especially selected from the group consisting of dimethylformamide, dimethylacetamide.

Thio compounds are especially selected from the group consisting of dimethyl sulphoxide, sulpholane.

Carboxylic acids are especially selected from the group consisting of formic acid, acetic acid, propionic acid, butanoic acid, pentanoic acid.

Alcohols are especially selected from the group consisting of
methanol, ethanol, propanol, iso-propanol, propane-1,2-diol, propane-1,3-diol, glycerol, butanol, sec-butanol, iso-butanol, tert-butanol, butane-1,2-diol, butane-1,3-diol, butane-1,4-diol, pentan-1-ol, pentan-2-ol, pentan-3-ol, tert-amyl alcohol, pentane-1,2-diol, pentane-1,3-diol, pentane-1,4-diol, pentane-1,5-diol, cyclopentanol, hexanol, cyclohexanol, heptanol, octanol, nonanol, decanol, ethylene glycol, diethylene glycol, triethylene glycol, polyethylene glycol, benzyl alcohol, phenol; preferably selected from methanol, ethanol, n-propanol, isopropanol; preferably methanol.

The process according to the invention can be conducted continuously or non-continuously, i.e. batchwise.

The reaction time depends on the progress of the process and on the desired conversion—the aim is typically a maximum possible conversion and the process according to the invention is continued until no further conversion of reactant can be observed.

The temperature in the process according to the invention is not restricted and is preferably in the range from 20° C. to 350° C., more preferably in the range from 50° C. to 300° C., even more preferably in the range from 50° C. to 250° C., most preferably in the range from 70° C. to 200° C., even more preferably 80° C. to 140° C.

The pressure in the process according to the invention is not restricted and is preferably in the range from 2 bar to 500 bar, more preferably in the range from 5 bar to 350 bar, even more preferably in the range from 15 bar to 300 bar, even more preferably 20 to 42 bar.

The above temperature ranges and pressure ranges may of course also be present in combination. Thus, the process can preferably be conducted at a temperature in the range from 20° C. to 350° C., [more preferably in the range from 50° C. to 300° C., even more preferably in the range from 50° C. to 250° C., most preferably in the range from 70° C. to 200° C., even more preferably at 80° C.-140° C.] and a pressure in the range from 2 bar to 500 bar [preferably in the range from 2 bar to 500 bar, more preferably in the range from 5 bar to 350 bar, even more preferably in the range from 15 bar to 300 bar, even more preferably 20 to 42 bar].

This process solves the problems addressed by the invention. It is particularly advantageous that the only by-product that arises in the reaction is water. In addition, the small excess of formaldehyde can either be converted to methanol by hydrogenation or removed by distillation and optionally recycled.

The workup of the crude product is therefore very simple: the catalyst is removed by filtration (it would also be conceivable in technical terms to use a fixed bed catalyst, such that this step would not be needed either), then the crude product is purified by distillation. The distillation affords only methanol (which can be recycled), water, the product and possibly formaldehyde (which can likewise be recycled).

By contrast with the related art processes, there is thus no need for any separation from the salts formed (which is generally effected by extraction with an additional solvent); in addition, the salts mentioned (or the aqueous solution thereof) are not obtained as a waste stream.

It is additionally advantageous in the process according to the invention that, in addition to the introduction of the methyl group on the piperidine nitrogen ($N^1$), it is also possible to simultaneously methylate other amino groups as well. For example, $N^4$-alkyl-4-amino-2,2,6,6-tetramethylpiperidines can be converted selectively to the $N^1,N^4$-dimethyl-$N^4$-alkyl-4-amino-2,2,6,6-tetramethylpiperidines. In this case, two or more methyl groups are thus introduced simultaneously (see Example I2).

A further advantage is that the presence of tertiary amino groups is also tolerated, without conversion thereof to the quaternary ammonium salts (see Example I3).

Having generally described this invention, a further understanding can be obtained by reference to certain specific examples which are provided herein for purposes of illustration only, and are not intended to be limiting unless otherwise specified.

The examples which follow are intended to illustrate the invention in detail, without any intention that the invention be restricted to these embodiments.

Examples

Paraformaldehyde was acquired from Sigma-Aldrich (95% purity).

The 37% by weight formalin solution used was acquired from Sigma-Aldrich.

The reactants utilized in examples I1 to I12 were those sold by Evonik Industries AG.

The reactant used in example I13 was obtained from Cytec (product name: Cyasorb 3346).

The reactant used in example I14 was obtained from Beijing Huashan Auxiliary (product name: Tinuvin 770).

The Pd/activated carbon catalyst used was that sold by Evonik Industries AG (product name: E 196 NN/W 10%).

Inventive Examples I1-I10

A 2 l pressure autoclave was charged with 1.5 mol of the particular triacetonamine compound ("reactant" according to Table 1), 3 mmol of palladium (as Pd/activated carbon catalyst) and 400 ml of methanol. Thereafter, an aqueous solution of formaldehyde (37% by weight of formaldehyde, where the % figure should be understood as being based on the total weight of the solution, i.e. 100 g of solution contain 37 g of formaldehyde) was added in the amount according to Table 1 and the reactor was closed.

Hydrogen was injected while stirring (40 bar $H_2$). Hydrogenation was effected at a temperature of 80 to 140° C. and a pressure of 20 to 42 bar until no significant uptake of hydrogen was observed any longer.

The reactor was then cooled and decompressed. The crude product was discharged and filtered, and then the solvent was first removed (80-120° C., standard pressure). Then, by gas chromatography (=GC, Agilent 5890 or 7890, FID detector), the yield of product and of any by-product(s) (I2, I3, I7, I9, I10) in the crude product obtained was determined (see Table 1, structures in the "Crude product" column). In the case of Examples I1 to I6, the residue was additionally purified by means of a vacuum distillation and the yield of main product was determined by GC.

The results are compiled in Table 1.

Inventive Examples I11-I14

A 1 l pressure autoclave was charged with the amount of the particular triacetonamine compound specified in Table 2 ("reactant" according to Table 2), 0.2 mol % of Pd (mol % based on the amount of the reactant) as Pd/activated carbon catalyst, and 250 ml of solvent (methanol or toluene). Thereafter, paraformaldehyde was added in the amount according to Table 2 and rinsed in with 50 ml of solvent, and the reactor was closed. Hydrogen was injected while stirring (40 bar $H_2$). Hydrogenation was effected at a temperature of 80 to 140° C. and a pressure of 20 to 42 bar until no significant uptake of hydrogen was observed any longer. The reactor was then cooled and decompressed. The crude product was discharged and filtered, and then the solvent was first removed (80-120° C., standard pressure). Then the yield of product in the crude product obtained was determined by gas chromatography (=GC, Agilent 5890 or 7890, FID detector) in the case of Examples I11, I12, I14, and by means of MS-ESI in the case of Example I13 (see Table 2, structures in the "crude product" column). In the case of Example I11, the residue was then purified as far as possible by means of a vacuum distillation.

The results are compiled in Table 2.

TABLE 1

| Example No. | Structure of reactant<br>(i) molar mass of reactant<br>(ii) amount of reactant used in g [or mol] | Aqueous formalin solution (37% by weight of formaldehyde)<br>(i) amount of formalin solution used (37% by weight of formaldehyde in water) in g<br>(ii) amount of formaldehyde used in mol<br>(iii) molar equivalents [= "mol. eq."] of formaldehyde, based on reactant | Crude product Structure | Crude product GC analysis Area % | Pure product GC analysis Content [area %] | Pure product Yield Pure fraction [%, based on the amount of reactant used in mol] |
|---|---|---|---|---|---|---|
| I1 | 4-propylamino-2,2,6,6-tetramethylpiperidine<br>(i) 212.4 g/mol<br>(ii) 321.4 g [1.5 mol] | (i) 267.8 g<br>(ii) 3.30 mol<br>(iii) 2.2 mol. eq. | 4-(N-methyl-N-propylamino)-1,2,2,6,6-pentamethylpiperidine | 97.9 | 98.3 | 93.7 |
| I2 | 4-propylamino-2,2,6,6-tetramethylpiperidine<br>(i) 212.4 g/mol<br>(ii) 321.4 g [1.5 mol] | (i) 133.9 g<br>(ii) 1.65 mol<br>(iii) 1.1 mol. eq. | 4-(N-methyl-N-propylamino)-2,2,6,6-tetramethylpiperidine | 88.6 | 99.4 | 77.8 |
| | | | By-product: 4-(N-methyl-N-propylamino)-1,2,2,6,6-pentamethylpiperidine | 10.4 | | |

TABLE 1-continued
| | | | | | |
|---|---|---|---|---|---|
| I3 | 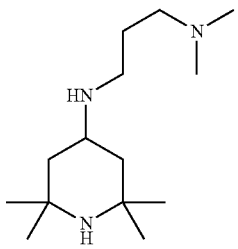 (i) 241.4 g/mol (ii) 362.1 g [1.50 mol] | (i) 267.8 g (ii) 3.30 mol (iii) 2.2 mol. eq. | 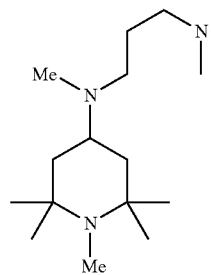 By-product: 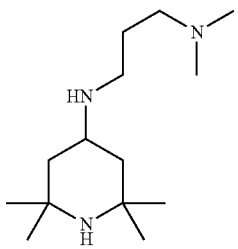 | 86.8 12.5 | 99.7 | 61.8 |
| I4 | 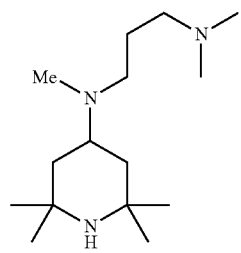 (i) 241.4 g/mol (ii) 365.4 g [1.51 mol] | (i) 121.7 g (ii) 1.50 mol (iii) 1.0 mol. eq. | 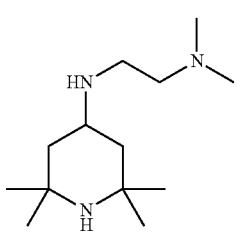 | 97.6 | 98.8 | 82.2 |
| I5 | 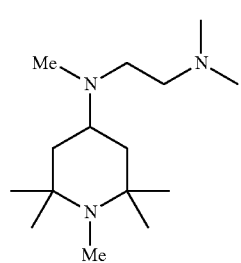 (i) 227.4 g/mol (ii) 341.8 g [1.50 mol] | (i) 316.5 g (ii) 3.90 mol (iii) 2.6 mol. eq. | 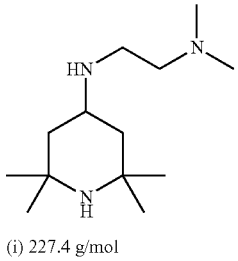 | 97.5 | 99.9 | 72.4 |
| I6 | 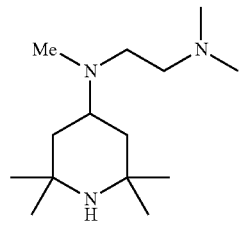 (i) 227.4 g/mol (ii) 178.0 g [0.78 mol] | (i) 63.3 g (ii) 0.78 mol (iii) 1.0 mol. eq. | | 98.9 | 98.8 | 86.7 |

TABLE 1-continued

| | Starting material | Parameters | Product | Yield (%) | | |
|---|---|---|---|---|---|---|
| I7 | 4-amino-2,2,6,6-tetramethylpiperidine<br>(i) 156.3 g/mol<br>(ii) 238.0 g [1.5 mol] | (i) 401.8 g<br>(ii) 4.95 mol<br>(iii) 3.3 mol. eq. | 4-(dimethylamino)-1,2,2,6,6-pentamethylpiperidine | 76.0 | 99.3 | 58.3 |
| | | | By-product: 4-(dimethylamino)-2,2,6,6-tetramethylpiperidine | 21.5 | | |
| I8 | 4-hydroxy-2,2,6,6-tetramethylpiperidine<br>(i) 157.3 g/mol<br>(ii) 157.0 g<br>(iii) 1.0 mol | (i) 89.3 g<br>(ii) 1.10 mol<br>(iii) 1.1 mol. eq. | 4-hydroxy-1,2,2,6,6-pentamethylpiperidine | 98.5 | — | — |
| I9 | N,N'-bis(2,2,6,6-tetramethylpiperidin-4-yl)-1,6-hexanediamine<br>(i) 394.7 g/mol<br>(ii) 198.3 g [0.5 mol] | (i) 89.2 g<br>(ii) 1.10 mol<br>(iii) 2.2 mol. eq. | N,N'-dimethyl-N,N'-bis(2,2,6,6-tetramethylpiperidin-4-yl)-1,6-hexanediamine | 80.4 | — | — |
| | | | By-products: N,N'-dimethyl-N,N'-bis(1,2,2,6,6-pentamethylpiperidin-4-yl)-1,6-hexanediamine (partially methylated) | 18.0 | | |
| | | | (fully methylated analog) | 1.1 | | |
| I10 | N,N'-bis(2,2,6,6-tetramethylpiperidin-4-yl)-1,6-hexanediamine<br>(i) 394.7 g/mol<br>(ii) 198.3 g [0.5 mol] | (i) 170.4 g<br>(ii) 2.10 mol<br>(iii) 4.2 mol. eq. | N,N'-dimethyl-N,N'-bis(1,2,2,6,6-pentamethylpiperidin-4-yl)-1,6-hexanediamine | 90.5 | — | — |

TABLE 1-continued

| | By-products: | 8.3 |
|---|---|---|
| | 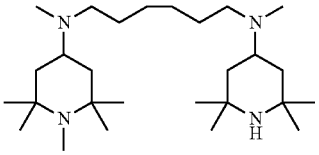 | |

TABLE 2

| Example No. | Structure of reactant<br>(i) Molar mass of reactant<br>(ii) amount of reactant used in g [or mol] | Paraformaldehyde (95% purity)<br>(i) amount of paraformaldehyde used in g<br>(ii) amount of formaldehyde used in mol (calculated taking account of the purity of 95%)<br>(iii) molar equivalents [= "mol. eq."] of formaldehyde, based on reactant | Solvent | Crude product Structure | Crude product GC analysis Area % | Pure product Content [area %] | Pure product Pure fraction [%, based on the amount of reactant used in mol] |
|---|---|---|---|---|---|---|---|
| I11 | 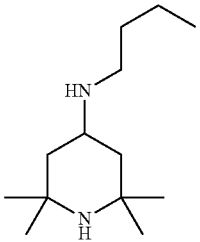<br>(i) 212.4 g/mol<br>(ii) 160.9 g<br>(iii) 0.76 mol | (i) 52.2 g<br>(ii) 1.65 mol<br>(iii) 2.2 mol. eq. | Methanol | 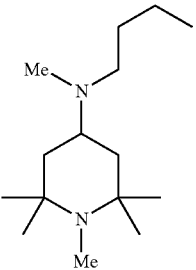 [SMILES: CCCCN(C)C1CC(C)(C)N(C)C(C)(C)C1] | 97.9 | 98.3 | 93.7 |
| I12 | 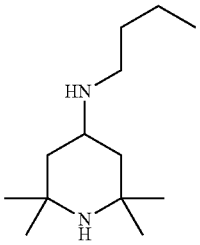<br>(i) 212.4 g/mol<br>(ii) 160.9 g<br>(iii) 0.76 mol | (i) 52.2 g<br>(ii) 1.65 mol<br>(iii) 2.2 mol. eq. | toluene | 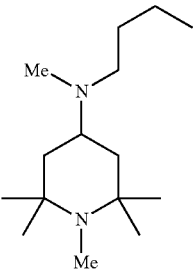 [SMILES: CCCCN(C)C1CC(C)(C)N(C)C(C)(C)C1] | 99.6 | — | — |

TABLE 2-continued

| I13 | Polymer formed from 1,6-N¹,N⁶-bis(2,2,6,6-tetramethyl-4-piperidinyl)-hexanediamine with 2,4-dichloro-6-(4-morpholinyl)-1,3,5-triazine (CAS No: 082451-48-7); Monomer Unit: [structure] (i) 558.8 g/mol of monomer unit (ii) 167.0 g [0.3 mol of monomer units] | (i) 20.9 g (ii) 0.66 mol (iii) 2.2 mol. eq. per monomer unit | toluene | [structure] | MS-ESI shows complete conversion | — | 95.0 |
| I14 | [structure] (i) 480.7 g/mol (ii) 241.1 g [0.50 mol] | (i) 34.8 g (ii) 1.10 mol (iii) 2.2 mol. eq. | MeOH | [structure] | 94.1 | — | — |

European patent application 15152068.1 filed Jan. 22, 2015, is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A process for preparing at least one N-methyl-substituted triacetonamine compound, comprising:

reacting at least one triacetonamine compound (I) with formaldehyde under reductive conditions, wherein the reductive conditions comprise reacting the at least one triacetonamine compound (I) with formaldehyde in the presence of hydrogen and a supported catalyst comprising at least one metal M selected from the group consisting of V, Cr, Mo, Mn, Ni, Pd, Pt, Fe, Ru, Os, Co, Rh, Ir, and Cu, and the triacetonamine compound (I) is selected from the group consisting of the chemical structures (I-B), (I-C), (I-D), (I-E), (I-F), (I-G), and (I-H)

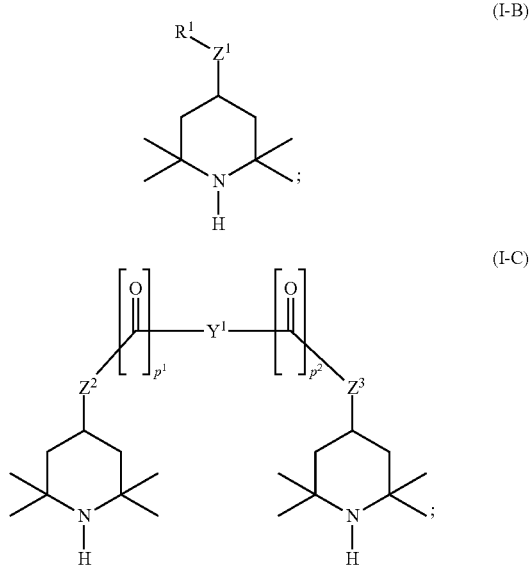

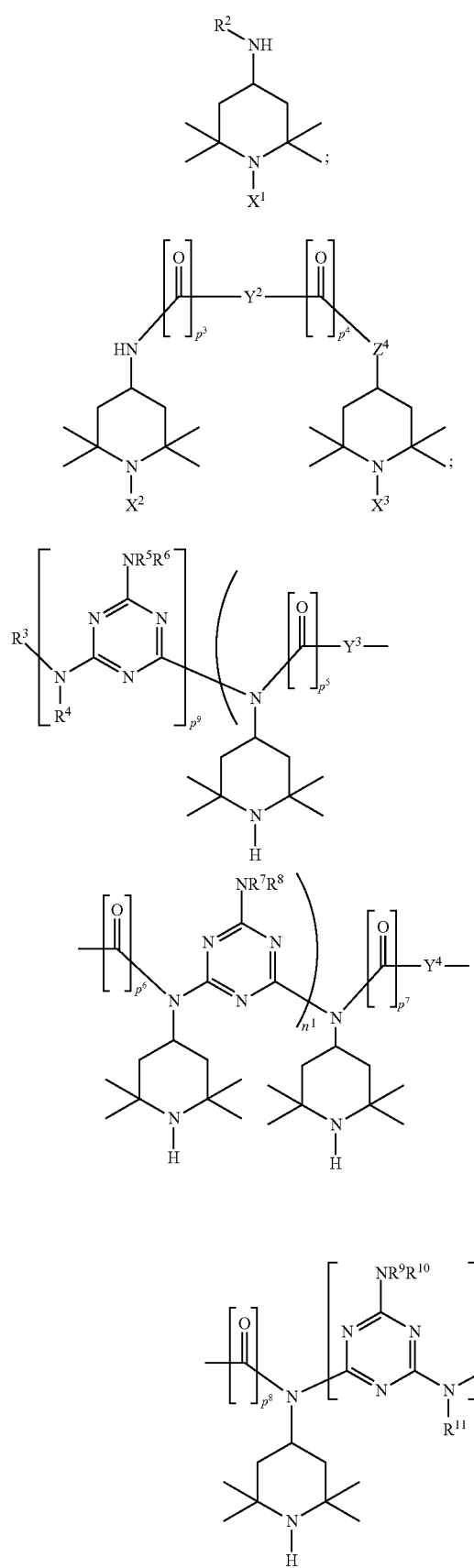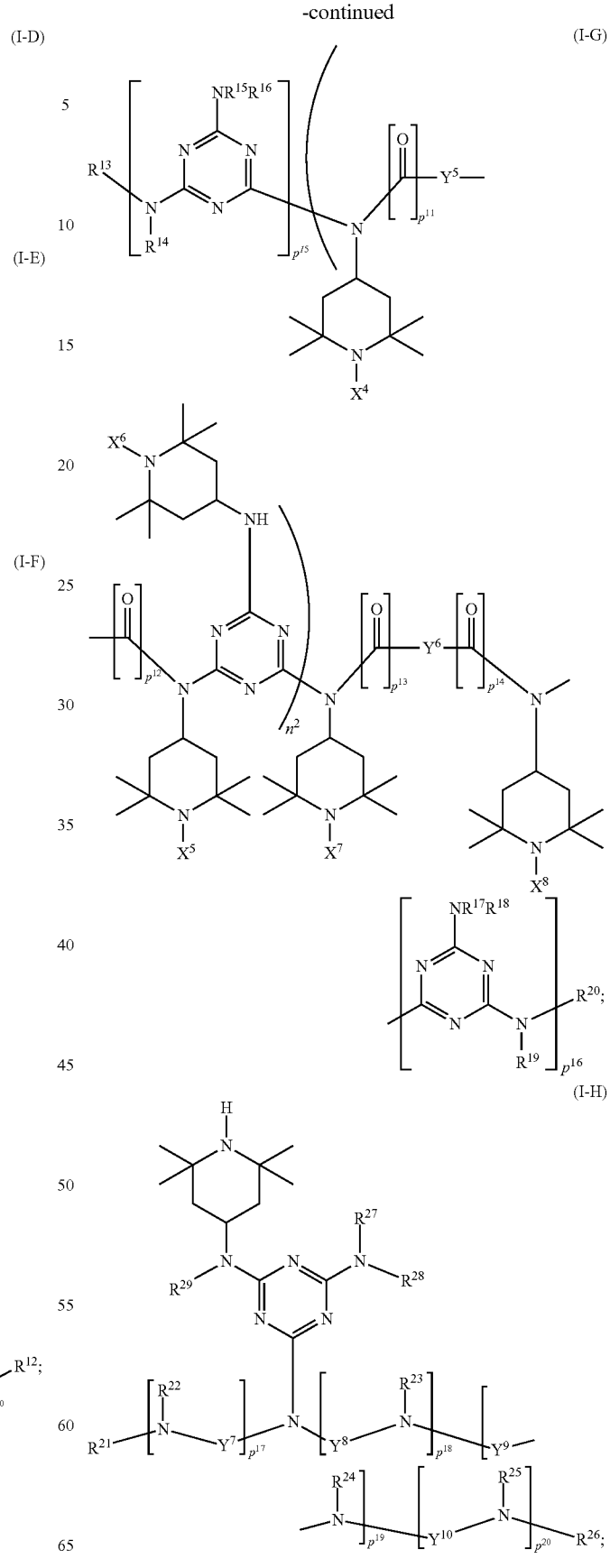

wherein $n^1$, $n^2$ are each independently an integer from the range of 1 to 20;

wherein $p^1$, $p^2$, $p^3$, $p^4$, $p^5$, $p^6$, $p^7$, $p^8$, $p^9$, $p^{10}$, $p^{11}$, $p^{12}$, $p^{13}$, $p^{14}$, $p^{15}$, $p^{16}$, $p^{17}$, $p^{18}$, $p^{19}$, $p^{20}$ are each independently 0 or 1;

wherein $X^1$ is selected from the group consisting of OH, —O., unbranched or branched alkyl group having 1 to 10 carbon atoms, and unbranched or branched alkoxy group having 1 to 10 carbon atoms;

wherein $X^2$, $X^3$ are each independently selected from the group consisting of hydrogen, OH, —O., unbranched or branched alkyl group having 1 to 10 carbon atoms, and unbranched or branched alkoxy group having 1 to 10 carbon atoms, and wherein $X^2$, $X^3$ are each selected independently, with the exclusion of: $X^2=X^3=$hydrogen;

wherein $X^4$, $X^5$, $X^6$, $X^7$, $X^8$ are each independently selected from the group consisting of hydrogen, OH, —O., unbranched or branched alkyl group having 1 to 10 carbon atoms, and unbranched or branched alkoxy group having 1 to 10 carbon atoms;

wherein $Y^1$, $Y^2$, $Y^3$, $Y^4$, $Y^5$, $Y^6$, $Y^7$, $Y^8$, $Y^9$, $Y^{10}$ are each independently selected from the group consisting of
an unbranched or branched alkylene group having 1 to 30 carbon atoms,
a divalent saturated hydrocarbyl group having 3 to 30 carbon atoms and having at least one saturated ring comprising 3 to 30 carbon atoms,
a divalent hydrocarbyl group having 6 to 30 carbon atoms, of which at least 6 carbon atoms are present in an aromatic system and the other carbon atoms, which are optionally present, are saturated, and
a bridging radical having a chemical structure selected from the group consisting of (i), and (ii)

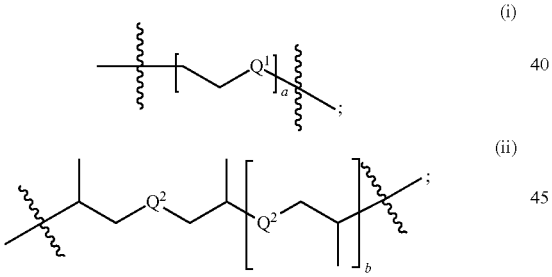

wherein
$Q^1$, $Q^2$ are each independently selected from the group consisting of —O—, —S—, —NH— and —NR'— with R'=unbranched or branched alkyl group having 1 to 6 carbon atoms,
wherein a is an integer selected from the range of 1 to 50,
wherein b is an integer selected from the range of 0 to 50, and wherein $Y^1$, if at least one of $p^1$ and $p^2$ has the value of 1, is selected from the group consisting of an unbranched or branched alkylene group having 1 to 30 carbon atoms; a divalent saturated hydrocarbyl group having 3 to 30 carbon atoms and having at least one saturated ring comprising 3 to 30 carbon atoms; a divalent hydrocarbyl group having 6 to 30 carbon atoms, of which at least 6 carbon atoms are present in an aromatic system and the other carbon atoms, which are optionally present, are saturated; a bridging radical having the chemical structure of (i) or (ii); and a direct bond, and wherein $Y^2$, if at least one of $p^3$ and $p^4$ has the value of 1, is selected from the group consisting of an unbranched or branched alkylene group having 1 to 30 carbon atoms; a divalent saturated hydrocarbyl group having 3 to 30 carbon atoms and having at least one saturated ring comprising 3 to 30 carbon atoms; a divalent hydrocarbyl group having 6 to 30 carbon atoms, of which at least 6 carbon atoms are present in an aromatic system and the other carbon atoms, which are optionally present, are saturated; a bridging radical having the chemical structure of (i) or (ii); and a direct bond, and wherein $Y^3$, if at least one of $p^5$ and $p^6$ has the value of 1, is selected from the group consisting of an unbranched or branched alkylene group having 1 to 30 carbon atoms, a divalent saturated hydrocarbyl group having 3 to 30 carbon atoms and having at least one saturated ring comprising 3 to 30 carbon atoms; a divalent hydrocarbyl group having 6 to 30 carbon atoms, of which at least 6 carbon atoms are present in an aromatic system and the other carbon atoms, which are optionally present, are saturated; a bridging radical having the chemical structure of (i) or (ii); and a direct bond, and wherein $Y^4$, if at least one of $p^7$ and $p^8$ has the value of 1, is selected from the group consisting of an unbranched or branched alkylene group having 1 to 30 carbon atoms, a divalent saturated hydrocarbyl group having 3 to 30 carbon atoms and having at least one saturated ring comprising 3 to 30 carbon atoms; a divalent hydrocarbyl group having 6 to 30 carbon atoms, of which at least 6 carbon atoms are present in an aromatic system and the other carbon atoms, which are optionally present, are saturated; a bridging radical having the chemical structure of (i) or (ii); and a direct bond, and wherein $Y^5$, if at least one of $p^{11}$ and $p^{12}$ has the value of 1, is selected from the group consisting of an unbranched or branched alkylene group having 1 to 30 carbon atoms; a divalent saturated hydrocarbyl group having 3 to 30 carbon atoms and having at least one saturated ring comprising 3 to 30 carbon atoms; a divalent hydrocarbyl group having 6 to 30 carbon atoms, of which at least 6 carbon atoms are present in an aromatic system and the other carbon atoms, which are optionally present, are saturated; a bridging radical having the chemical structure of (i) or (ii); and a direct bond, and wherein $Y^6$, if at least one of $p^{13}$ and $p^{14}$ has the value of 1, is selected from the group consisting of an unbranched or branched alkylene group having 1 to 30 carbon atoms; a divalent saturated hydrocarbyl group having 3 to 30 carbon atoms and having at least one saturated ring comprising 3 to 30 carbon atoms; a divalent hydrocarbyl group having 6 to 30 carbon atoms, of which at least 6 carbon atoms are present in an aromatic system and the other carbon atoms, which are optionally present, are saturated; a bridging radical having the chemical structure of (i) or (ii); and a direct bond, and wherein $Z^1$, $Z^2$, $Z^3$, $Z^4$ are each independently selected from the group consisting of —O—, —S—, and —$NR^{30}$—;

wherein the $R^1$, $R^2$, $R^3$, $R^4$, $R^5$, $R^6$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{30}$ radicals are each independently selected from the group consisting of
hydrogen,
an unbranched or branched alkyl group which has 1 to 30 carbon atoms and in which at least one hydrogen radical may be replaced by a radical selected from the group consisting of —OH, —$NH_2$, —$OCH_3$, —$OCH_2CH_3$, —$NH(CH_3)$, —$N(CH_3)_2$, —$NH(CH_2CH_3)$, —$N(CH_2CH_3)_2$, and —$N(CH_3)(CH_2CH_3)$,
an unbranched or branched acyl group which has 1 to 30 carbon atoms and in which at least one hydrogen radical may be replaced by a radical selected from the group consisting of —OH, —$NH_2$, —$OCH_3$, —$OCH_2CH_3$, —$NH(CH_3)$, —$N(CH_3)_2$, —$NH(CH_2CH_3)$, —$N(CH_2CH_3)_2$, and —$N(CH_3)(CH_2CH_3)$, and
a radical having a chemical structure selected from the group consisting of (iii), (iv), (v), (vi), (vii), (viii), and (ix)

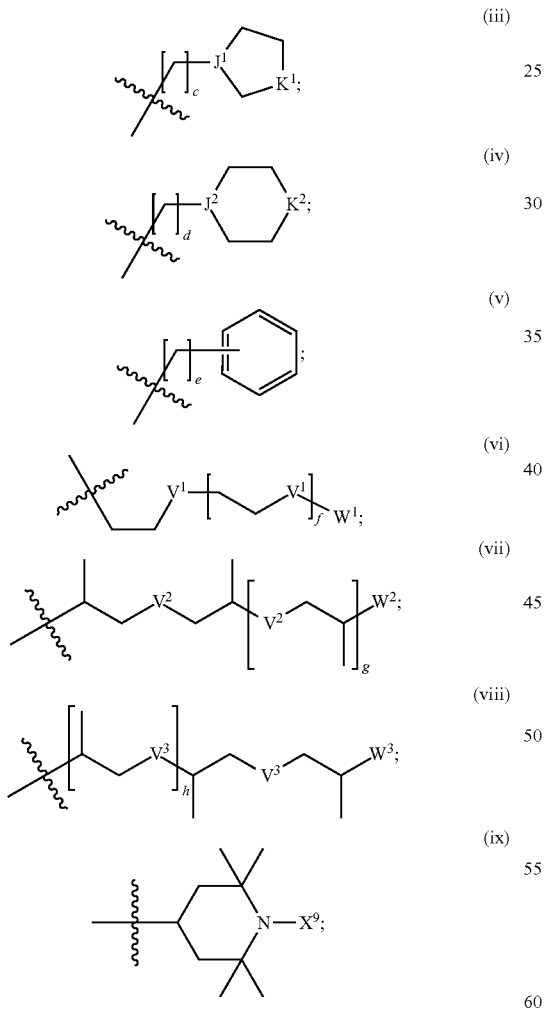

wherein $J^1$, $J^2$ are each independently selected from the group consisting of CH, and N,
wherein $K^1$, $K^2$ are each independently selected from the group consisting of —O—, —NH—, —N($CH_3$)—, —N($CH_2CH_3$)—, —S—, and —$CH_2$—, wherein $V^1$, $V^2$, $V^3$ are each independently selected from the group consisting of —O—, —S—, —NH—, and —NR"— with R"=unbranched or branched alkyl group having 1 to 6 carbon atoms,
wherein $W^1$, $W^2$, $W^3$ are each independently selected from the group consisting of H, methyl, and ethyl,
wherein c, d, e, f, g, h are each independently an integer from the range of 0 to 50,
wherein $X^9$ is selected from the group consisting of hydrogen, —OH, —O., an unbranched or branched alkyl group having 1 to 10 carbon atoms, and an unbranched or branched alkoxy group having 1 to 10 carbon atoms,
wherein, in the chemical structures (iii), (iv), (v), (vi), (vii), (viii), (ix), at least one hydrogen radical bonded to a carbon atom may be replaced by a radical selected from the group consisting of
—OH, —$NH_2$, —$OCH_3$, —$OCH_2CH_3$, —$NH(CH_3)$, —$N(CH_3)_2$, —$NH(CH_2CH_3)$, —$N(CH_2CH_3)_2$, and —$N(CH_3)(CH_2CH_3)$;
wherein the $R^7$, $R^8$ radicals are each independently selected from the group consisting of
hydrogen,
an unbranched or branched alkyl group which has 1 to 30 carbon atoms and in which at least one hydrogen radical may be replaced by a radical selected from the group consisting of —OH, —$NH_2$, —$OCH_3$, —$OCH_2CH_3$, —$NH(CH_3)$, —$N(CH_3)_2$, —$NH(CH_2CH_3)$, —$N(CH_2CH_3)_2$, and —$N(CH_3)(CH_2CH_3)$, and
an unbranched or branched acyl group which has 1 to 30 carbon atoms and in which at least one hydrogen radical may be replaced by a radical selected from the group consisting of —OH, —$NH_2$, —$OCH_3$, —$OCH_2CH_3$, —$NH(CH_3)$, —$N(CH_3)_2$, —$NH(CH_2CH_3)$, —$N(CH_2CH_3)_2$, and —$N(CH_3)(CH_2CH_3)$;
and wherein, —$NR^3R^4$, if $p^9$=1, is selected from the list above including a radical of the chemical structure (x),
and wherein, —$NR^{11}R^{12}$, if $p^{10}$=1, is selected from the list above including a radical of the chemical structure (x),
and wherein the —$NR^5R^6$, —$NR^7R^8$, —$NR^9R^{10}$ radicals are each independently selected from the list above including a radical of the chemical structure (x),
wherein the chemical structure (x) is:

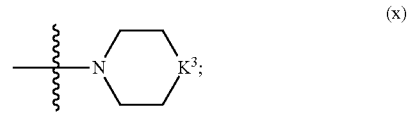

wherein $K^3$ is selected from the group consisting of —O—, —S—, —NH—, —N($CH_3$)—, and —N($CH_2CH_3$)—;
wherein the $R^{21}$, $R^{22}$, $R^{23}$, $R^{24}$, $R^{25}$, $R^{26}$ radicals are each independently selected from the group consisting of
hydrogen,
an unbranched or branched alkyl group having 1 to 30 carbon atoms, and a group having the chemical structure (xi)

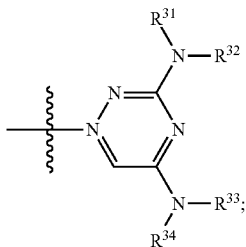

wherein the $R^{27}$, $R^{28}$, $R^{29}$, $R^{31}$, $R^{32}$, $R^{33}$, $R^{34}$ radicals are each independently selected from the group consisting of hydrogen, an unbranched or branched alkyl group which has 1 to 30 carbon atoms and in which at least one hydrogen radical may be replaced by a radical selected from the group consisting of —OH, —$NH_2$, —$OCH_3$, —$OCH_2CH_3$, —$NH(CH_3)$, —$N(CH_3)_2$, —$NH(CH_2CH_3)$, —$N(CH_2CH_3)_2$, and —$N(CH_3)(CH_2CH_3)$, an unbranched or branched acyl group which has 1 to 30 carbon atoms and in which at least one hydrogen radical may be replaced by a radical selected from the group consisting of —OH, —$NH_2$, —$OCH_3$, —$OCH_2CH_3$, —$NH(CH_3)$, —$N(CH_3)_2$, —$NH(CH_2CH_3)$, —$N(CH_2CH_3)_2$, and —$N(CH_3)(CH_2CH_3)$; and a radical having a chemical structure selected from the group consisting of (xii), (xiii), (xiv), (xv), (xvi), (xvii), and (xviii)

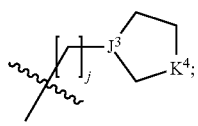

(xii)

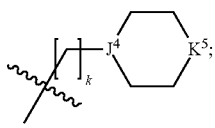

(xiii)

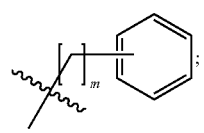

(xiv)

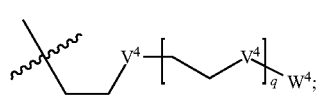

(xv)

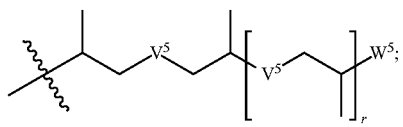

(xvi)

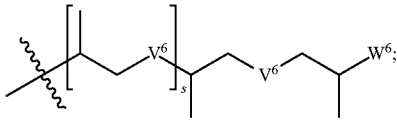

(xvii)

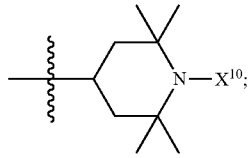

(xviii)

wherein $J^3$, $J^4$ are each independently selected from the group consisting of CH, and N, wherein $K^4$, $K^5$ are each independently selected from the group consisting of —O—, —NH—, —$N(CH_3)$—, —$N(CH_2CH_3)$—, —S—, and —$CH_2$—, wherein $V^4$, $V^5$, $V^6$ are each independently selected from the group consisting of —O—, —S—, —NH—, and —NR'''— with R'''=unbranched or branched alkyl group having 1 to 6 carbon atoms, wherein $W^4$, $W^5$, $W^6$ are each independently selected from the group consisting of H, methyl, and ethyl, wherein j, k, m, q, r, s are each independently an integer from the range of 0 to 50, wherein $X^{10}$ is selected from the group consisting of hydrogen, —OH, —O., an unbranched or branched alkyl group having 1 to 10 carbon atoms, and an unbranched or branched alkoxy group having 1 to 10 carbon atoms, wherein, in the chemical structures (xii), (xiii), (xiv), (xv), (xvi), (xvii), (xviii), at least one hydrogen radical bonded to a carbon atom may be replaced by a radical selected from the group consisting of —OH, —$NH_2$, —$OCH_3$, —$OCH_2CH_3$, —$NH(CH_3)$, —$N(CH_3)_2$, —$NH(CH_2CH_3)$, —$N(CH_2CH_3)_2$, and —$N(CH_3)(CH_2CH_3)$, and with the proviso that $R^{21}$ and $R^{26}$, when $p^{17}=p^{18}=p^{19}=p^{20}=0$, are each independently a group of the chemical structure (xix)

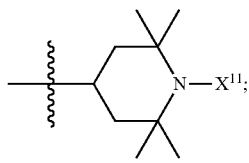

(xix)

wherein $X^{11}$ is selected from the group consisting of hydrogen, OH, —O., an unbranched or branched alkyl group having 1 to 10 carbon atoms, and an unbranched or branched alkoxy group having 1 to 10 carbon atoms.

2. The process according to claim 1, wherein $p^1=p^2=p^3=p^4=p^5=p^6=p^7=p^8=p^{11}=p^{12}=p^{13}=p^{14}=0$, and $p^9$, $p^{10}$, $p^{15}$, $p^{16}$, $p^{17}$, $p^{18}$, $p^{19}$, $p^{20}$ are each independently 0 or 1.

3. The process according to claim 1, wherein $Y^1$, $Y^2$, $Y^3$, $Y^4$, $Y^5$, $Y^6$, $Y^7$, $Y^8$, $Y^9$, $Y^{10}$ are each independently selected from the group consisting of an unbranched or branched alkylene group having 1 to 30 carbon atoms, and a divalent saturated hydrocarbyl group having 3 to 30 carbon atoms and having at least one saturated ring comprising 3 to 30 carbon atoms.

4. The process according to claim 1, wherein the $R^1$, $R^2$, $R^3$, $R^4$, $R^5$, $R^6$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{30}$ radicals are each independently selected from the group consisting of hydrogen, an unbranched or branched alkyl group which has 1 to 30 carbon atoms and in which at least one hydrogen radical may be replaced by a radical selected from the group consisting of —OH, —$NH_2$, —$OCH_3$, —$OCH_2CH_3$, —$NH(CH_3)$, —$N(CH_3)_2$, —NH($CH_2CH_3$), —$N(CH_2CH_3)_2$, and —$N(CH_3)(CH_2CH_3)$, and a radical having a chemical structure (ix) with

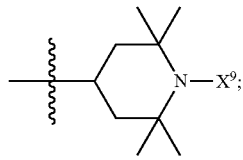

(ix)

wherein $X^9$ is selected from the group consisting of hydrogen, —OH, —O., unbranched or branched alkyl group having 1 to 10 carbon atoms, and unbranched or branched alkoxy group having 1 to 10 carbon atoms;

wherein the $R^7$, $R^8$ radicals are each independently selected from the group consisting of hydrogen, and an unbranched or branched alkyl group which has 1 to 30 carbon atoms and in which at least one hydrogen radical may be replaced by a radical selected from the group consisting of —OH, —$NH_2$, —$OCH_3$, —$OCH_2CH_3$, —$NH(CH_3)$, —$N(CH_3)_2$, —NH($CH_2CH_3$), —$N(CH_2CH_3)_2$, and —$N(CH_3)(CH_2CH_3)$, and wherein, —$NR^3R^4$, if $p^9$=1, is selected from the list above including a radical of the chemical structure (x), and wherein, —$NR^{11}R^{12}$, if $p^{10}$=1, is selected from the list above including a radical of the chemical structure (x), and wherein the —$NR^5R^6$, —$NR^7R^8$, —$NR^9R^{10}$ radicals are each independently selected from the list above including a radical of the chemical structure (x), wherein the chemical structure (x) is:

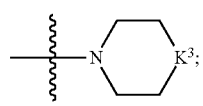

(x)

wherein $K^3$ is selected from the group consisting of —O—, —S—, —NH—, —N($CH_3$)—, and —N($CH_2CH_3$)—;

wherein the $R^{21}$, $R^{22}$, $R^{23}$, $R^{24}$, $R^{25}$, $R^{26}$ radicals are each independently selected from the group consisting of hydrogen, an unbranched or branched alkyl group having 1 to 30 carbon atoms, and a group having the chemical structure (xi)

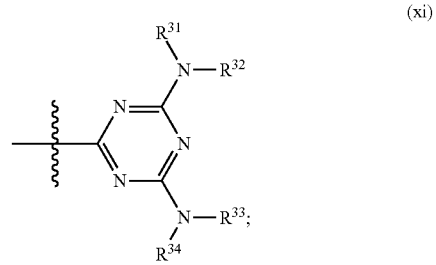

(xi)

wherein the $R^{27}$, $R^{28}$, $R^{29}$, $R^{31}$, $R^{32}$, $R^{33}$, $R^{34}$ radicals are each independently selected from the group consisting of hydrogen, an unbranched or branched alkyl group which has 1 to 30 carbon atoms and in which at least one hydrogen radical may be replaced by a radical selected from the group consisting of —OH, —$NH_2$, —$OCH_3$, —$OCH_2CH_3$, —$NH(CH_3)$, —$N(CH_3)_2$, —NH($CH_2CH_3$), —$N(CH_2CH_3)_2$, and —$N(CH_3)(CH_2CH_3)$, and a radical having a chemical structure (xviii)

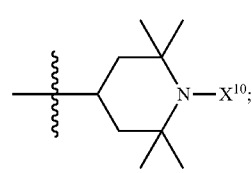

(xviii)

wherein $X^{10}$ is selected from the group consisting of hydrogen, —OH, —O., an unbranched or branched alkyl group having 1 to 10 carbon atoms, and an unbranched or branched alkoxy group having 1 to 10 carbon atoms, and with the proviso that $R^{21}$ and $R^{26}$, when $p^{17}$=$p^{18}$=$p^{19}$=$p^{20}$=0, are each independently a group of the chemical structure (xix)

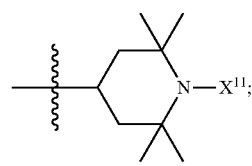

(xix)

wherein $X^{11}$ is selected from the group consisting of hydrogen, OH, —O., an unbranched or branched alkyl group having 1 to 10 carbon atoms, and an unbranched or branched alkoxy group having 1 to 10 carbon atoms.

5. The process according to claim 1, wherein $X^4$=$X^5$=$X^6$=$X^7$=$X^8$=$X^9$=$X^{10}$=$X^{11}$=hydrogen.

6. The process according to claim 1, wherein the triacetonamine compound (I) is selected from the group consisting of the chemical structures (I-B), (I-C), (I-D), and (I-E).

7. The process according to claim 6, wherein the triacetonamine compound (I) is selected from the group consisting of the chemical structures (I-B) and (I-D), and wherein $Z^1$ is selected from the group consisting of —O—, —S—, and —NR$^{30}$—;

wherein the $R^1$, $R^2$, $R^{30}$ radicals are each independently selected from the group consisting of hydrogen, and an unbranched or branched alkyl group which has 1 to 30 carbon atoms and in which at least one hydrogen radical may be replaced by a radical selected from the group consisting of —OH, —NH$_2$, —OCH$_3$, —OCH$_2$CH$_3$, —NH(CH$_3$), —N(CH$_3$)$_2$, —NH(CH$_2$CH$_3$), —N(CH$_2$CH$_3$)$_2$, and —N(CH$_3$)(CH$_2$CH$_3$).

8. The process according to claim 7, wherein the triacetonamine compound (I) is selected from the group consisting of the chemical structures (I-B) and (I-D), and wherein $Z^1$ is selected from the group consisting of –O—, and —NR$^{30}$—;

wherein the $R^1$, $R^2$, $R^{30}$ radicals are each independently selected from the group consisting of hydrogen, and an unbranched or branched alkyl group having 1 to 12 carbon atoms.

9. The process according to claim 1, wherein formaldehyde is in a form of a gas, an aqueous solution, or a solid.

10. The process according to claim 1, wherein the reacting of the at least one triacetonamine compound (I) with formaldehyde occurs in a solvent, wherein the solvent is at least one selected from the group consisting of an aliphatic solvent, an aromatic solvent, an ether, a halogenated solvent, an amide, a thio compound, a carboxylic acid, an alcohol, and water.

11. The process according to claim 1, wherein the reacting of the at least one triacetonamine compound (I) with formaldehyde occurs at a temperature in the range of from 20° C. to 350° C. and a pressure in the range of from 2 bar to 500 bar.

12. The process according to claim 1, wherein, in the supported catalyst, the at least one metal M is applied on a support selected from the group consisting of activated carbon, calcium carbonate, aluminium oxide, and titanium dioxide.

13. The process according to claim 1, wherein the solvent comprises at least one of toluene and methanol.

14. The process according to claim 1, wherein the reacting of the at least one triacetonamine compound (I) with formaldehyde is carried out such that a reaction product other than the at least one N-methyl-substituted triacetonamine compound consists of water.

15. The process according to claim 1, wherein the at least one metal M is selected from the group consisting of Cr, Ni, Pd, and Pt.

16. The process according to claim 1, wherein at least one $N^1$-nitrogen of a 2,2,6,6-tetramethylpiperidine moiety of the triacetonamine compound (I) is substituted with a methyl group.

* * * * *